US009247977B2

(12) United States Patent
Fallin et al.

(10) Patent No.: US 9,247,977 B2
(45) Date of Patent: Feb. 2, 2016

(54) ROD CONTOURING APPARATUS FOR PERCUTANEOUS PEDICLE SCREW EXTENSION

(75) Inventors: T. Wade Fallin, Hyde Park, UT (US); Joshua A. Butters, Chandler, AZ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 804 days.

(21) Appl. No.: 12/316,637

(22) Filed: Dec. 15, 2008

(65) Prior Publication Data

US 2009/0099605 A1    Apr. 16, 2009

Related U.S. Application Data

(62) Division of application No. 11/526,785, filed on Sep. 25, 2006, now Pat. No. 8,894,655.

(60) Provisional application No. 60/765,606, filed on Feb. 6, 2006.

(51) Int. Cl.
*A61B 17/88* (2006.01)
*A61B 17/70* (2006.01)

(52) U.S. Cl.
CPC .............. *A61B 17/88* (2013.01); *A61B 17/7041* (2013.01); *A61B 17/7085* (2013.01); *A61B 17/8863* (2013.01); *A61B 17/7037* (2013.01); *A61B 17/8897* (2013.01)

(58) Field of Classification Search
CPC ............... A61B 17/70; A61B 17/7002; A61B 17/7011; A61B 17/7013
USPC .............................. 606/86 A, 90, 99, 246–278
See application file for complete search history.

(56) References Cited

U.S. PATENT DOCUMENTS

| 3,788,318 A | 1/1974 | Kim et al. |
| 3,789,852 A | 2/1974 | Kim et al. |

(Continued)

FOREIGN PATENT DOCUMENTS

| DE | 37 11 091 | 10/1988 |
| DE | 4238339 A1 | 5/1994 |

(Continued)

OTHER PUBLICATIONS

Office Action from U.S. Appl. No. 11/178,035, mailed Nov. 13, 2009.

(Continued)

*Primary Examiner* — Matthew Lawson
(74) *Attorney, Agent, or Firm* — Lerner, David, Littenberg, Krumholz & Mentlik, LLP

(57) ABSTRACT

Anatomic points within the body are projected outside the body through the use of extenders (180, 182, 188). The projected points may then be used for measurement, or to facilitate the selection or configuration of an implant that is positioned proximate the anatomic points using a slotted cannula (143). Such an implant may be a rod (270) for a posterior spinal fusion system. Pedicle screws (140, 142, 148) may be implanted into pedicles of the spine, and may then serve as anchors for the extenders. The extenders (180, 182, 188) may have rod interfaces (214, 216, 218) that receive the rod (270) in a manner that mimics the geometry of the pedicle screws (140, 142, 148) so that the selected or configured contoured rod (270) will properly fit into engagement with the pedicle screws (140, 142, 148).

23 Claims, 19 Drawing Sheets

(56) References Cited

U.S. PATENT DOCUMENTS

| | | | |
|---|---|---|---|
| 3,892,232 A | 7/1975 | Neufeld | |
| 4,083,370 A * | 4/1978 | Taylor | 604/156 |
| 4,350,151 A | 9/1982 | Scott | |
| 4,409,968 A | 10/1983 | Drummond | |
| 4,411,259 A | 10/1983 | Drummond | |
| 4,448,191 A | 5/1984 | Rodnyansky et al. | |
| 4,449,532 A | 5/1984 | Storz et al. | |
| 4,474,046 A | 10/1984 | Cook | |
| 4,545,374 A | 10/1985 | Jacobson | |
| 4,611,581 A | 9/1986 | Steffee | |
| 4,653,481 A | 3/1987 | Howland et al. | |
| 4,790,297 A | 12/1988 | Luque | |
| 4,817,587 A | 4/1989 | Janese | |
| 4,862,891 A | 9/1989 | Smith | |
| 4,887,595 A | 12/1989 | Heinig et al. | |
| 4,899,729 A | 2/1990 | Gill et al. | |
| 4,913,134 A | 4/1990 | Luque | |
| 4,957,495 A | 9/1990 | Kluger | |
| 5,010,879 A | 4/1991 | Moriya et al. | |
| 5,027,793 A | 7/1991 | Engelhardt et al. | |
| 5,125,396 A | 6/1992 | Ray | |
| 5,171,279 A | 12/1992 | Mathews | |
| 5,183,464 A | 2/1993 | Dubrul et al. | |
| 5,195,541 A | 3/1993 | Obenchain | |
| 5,242,443 A | 9/1993 | Kambin | |
| 5,295,994 A | 3/1994 | Bonutti | |
| D346,217 S | 4/1994 | Sparker et al. | |
| 5,357,983 A | 10/1994 | Mathews | |
| 5,360,431 A | 11/1994 | Puno et al. | |
| 5,373,860 A | 12/1994 | Catone | |
| 5,395,317 A | 3/1995 | Kambin | |
| 5,409,488 A | 4/1995 | Ulrich | |
| 5,425,732 A | 6/1995 | Ulrich | |
| 5,439,464 A | 8/1995 | Shapiro | |
| 5,480,440 A | 1/1996 | Kambin | |
| 5,490,409 A | 2/1996 | Weber | |
| 5,496,322 A | 3/1996 | Mathews | |
| 5,545,228 A | 8/1996 | Kambin | |
| 5,569,248 A | 10/1996 | Mathews | |
| 5,569,290 A | 10/1996 | McAfee | |
| 5,584,887 A | 12/1996 | Kambin | |
| 5,591,165 A | 1/1997 | Jackson | |
| 5,601,590 A | 2/1997 | Bonutti et al. | |
| 5,624,442 A | 4/1997 | Mellinger et al. | |
| 5,658,286 A | 8/1997 | Sava | |
| 5,720,751 A | 2/1998 | Jackson | |
| 5,728,097 A | 3/1998 | Mathews | |
| 5,741,261 A | 4/1998 | Moskovitz et al. | |
| 5,746,720 A | 5/1998 | Stouder, Jr. | |
| 5,762,629 A | 6/1998 | Kambin | |
| 5,792,044 A | 8/1998 | Foley et al. | |
| 5,814,046 A | 9/1998 | Hopf | |
| 5,882,344 A | 3/1999 | Stouder, Jr. | |
| 5,885,291 A | 3/1999 | Moskovitz et al. | |
| 5,885,292 A | 3/1999 | Moskovitz et al. | |
| 5,891,147 A | 4/1999 | Moskovitz et al. | |
| 5,902,231 A | 5/1999 | Foley et al. | |
| RE36,221 E | 6/1999 | Breard et al. | |
| 5,928,139 A | 7/1999 | Koros et al. | |
| 5,938,662 A | 8/1999 | Rinner | |
| 5,944,658 A | 8/1999 | Koros et al. | |
| 5,954,635 A | 9/1999 | Foley et al. | |
| 5,957,888 A | 9/1999 | Hinchliffe | |
| 5,961,499 A | 10/1999 | Bonutti et al. | |
| 5,964,761 A | 10/1999 | Kambin | |
| 5,976,146 A | 11/1999 | Ogawa et al. | |
| 6,007,487 A | 12/1999 | Foley et al. | |
| 6,015,409 A | 1/2000 | Jackson | |
| 6,033,406 A | 3/2000 | Mathews | |
| 6,035,691 A | 3/2000 | Lin et al. | |
| 6,090,113 A | 7/2000 | Le Couedic et al. | |
| 6,123,707 A | 9/2000 | Wagner | |
| 6,127,597 A | 10/2000 | Beyar et al. | |
| 6,152,871 A | 11/2000 | Foley et al. | |
| 6,159,179 A | 12/2000 | Simonson | |
| 6,162,170 A | 12/2000 | Foley et al. | |
| 6,175,758 B1 | 1/2001 | Kambin | |
| 6,183,472 B1 | 2/2001 | Lutz | |
| 6,187,000 B1 | 2/2001 | Davison et al. | |
| 6,197,002 B1 | 3/2001 | Peterson | |
| 6,200,322 B1 | 3/2001 | Branch et al. | |
| 6,206,822 B1 | 3/2001 | Foley et al. | |
| 6,206,826 B1 | 3/2001 | Mathews et al. | |
| 6,217,509 B1 | 4/2001 | Foley et al. | |
| 6,226,548 B1 | 5/2001 | Foley et al. | |
| 6,235,028 B1 | 5/2001 | Brumfield et al. | |
| 6,287,313 B1 | 9/2001 | Sasso | |
| 6,332,780 B1 | 12/2001 | Traxel et al. | |
| 6,371,968 B1 | 4/2002 | Kogasaka et al. | |
| 6,425,859 B1 | 7/2002 | Foley et al. | |
| 6,485,518 B1 | 11/2002 | Cornwall et al. | |
| 6,506,151 B2 | 1/2003 | Estes et al. | |
| 6,520,907 B1 | 2/2003 | Foley et al. | |
| 6,524,320 B2 | 2/2003 | DiPoto | |
| 6,530,926 B1 | 3/2003 | Davison | |
| 6,530,929 B1 | 3/2003 | Justis et al. | |
| 6,562,046 B2 | 5/2003 | Sasso | |
| 6,575,979 B1 | 6/2003 | Cragg | |
| 6,596,008 B1 | 7/2003 | Kambin | |
| 6,605,095 B2 | 8/2003 | Grossman | |
| 6,607,530 B1 | 8/2003 | Carl et al. | |
| 6,723,095 B2 | 4/2004 | Hammerslag | |
| 6,740,089 B2 | 5/2004 | Haider | |
| 6,749,614 B2 | 6/2004 | Teitelbaum et al. | |
| 6,770,074 B2 | 8/2004 | Michelson | |
| 6,793,656 B1 | 9/2004 | Mathews | |
| 6,800,084 B2 | 10/2004 | Davison et al. | |
| 6,811,558 B2 | 11/2004 | Davison et al. | |
| 6,821,277 B2 | 11/2004 | Teitelbaum | |
| 6,837,891 B2 | 1/2005 | Davison et al. | |
| 6,849,064 B2 | 2/2005 | Hamada | |
| 6,875,212 B2 | 4/2005 | Shaolian et al. | |
| 6,899,713 B2 | 5/2005 | Shaolian et al. | |
| 6,923,811 B1 | 8/2005 | Carl et al. | |
| 6,929,647 B2 | 8/2005 | Cohen | |
| 6,964,667 B2 | 11/2005 | Shaolian et al. | |
| 7,008,422 B2 | 3/2006 | Foley et al. | |
| 7,008,424 B2 | 3/2006 | Teitelbaum | |
| 7,011,660 B2 | 3/2006 | Sherman et al. | |
| 7,083,621 B2 | 8/2006 | Shaolian et al. | |
| 7,160,300 B2 | 1/2007 | Jackson | |
| 7,188,626 B2 | 3/2007 | Foley et al. | |
| 7,250,052 B2 | 7/2007 | Landry et al. | |
| 7,306,603 B2 | 12/2007 | Boehm, Jr. et al. | |
| 7,758,617 B2 | 7/2010 | Iott et al. | |
| 7,811,288 B2 | 10/2010 | Jones et al. | |
| 7,927,360 B2 * | 4/2011 | Pond et al. | 606/265 |
| 7,955,355 B2 | 6/2011 | Chin | |
| 8,002,798 B2 | 8/2011 | Chin et al. | |
| 8,177,817 B2 | 5/2012 | Fallin | |
| 8,192,440 B2 | 6/2012 | Jones et al. | |
| 2001/0011170 A1 | 8/2001 | Davison et al. | |
| 2001/0027320 A1 | 10/2001 | Sasso | |
| 2001/0029353 A1 | 10/2001 | Peterson | |
| 2001/0049498 A1 | 12/2001 | Davison et al. | |
| 2001/0049527 A1 | 12/2001 | Cragg | |
| 2001/0053915 A1 | 12/2001 | Grossman | |
| 2002/0016583 A1 | 2/2002 | Cragg | |
| 2002/0045904 A1 | 4/2002 | Fuss et al. | |
| 2002/0068975 A1 | 6/2002 | Teitelbaum et al. | |
| 2002/0082598 A1 | 6/2002 | Teitelbaum | |
| 2002/0082600 A1 | 6/2002 | Shaolian et al. | |
| 2002/0107519 A1 | 8/2002 | Dixon et al. | |
| 2002/0116006 A1 | 8/2002 | Cohen | |
| 2002/0161367 A1 | 10/2002 | Ferree | |
| 2002/0161368 A1 | 10/2002 | Foley et al. | |
| 2002/0173796 A1 | 11/2002 | Cragg | |
| 2002/0198526 A1 | 12/2002 | Shaolian et al. | |
| 2003/0060824 A1 | 3/2003 | Viart et al. | |
| 2003/0060826 A1 | 3/2003 | Foley et al. | |
| 2003/0073998 A1 | 4/2003 | Pagliuca et al. | |
| 2003/0083688 A1 | 5/2003 | Simonson | |
| 2003/0139648 A1 | 7/2003 | Foley et al. | |
| 2003/0195518 A1 | 10/2003 | Cragg | |

(56) References Cited

U.S. PATENT DOCUMENTS

| | | |
|---|---|---|
| 2003/0199872 A1 | 10/2003 | Markworth et al. |
| 2003/0199884 A1 | 10/2003 | Davison et al. |
| 2003/0204189 A1 | 10/2003 | Cragg |
| 2003/0208202 A1 | 11/2003 | Falahee |
| 2003/0225408 A1 | 12/2003 | Nichols et al. |
| 2003/0229353 A1 | 12/2003 | Cragg |
| 2004/0006341 A1 | 1/2004 | Shaolian et al. |
| 2004/0006344 A1 | 1/2004 | Nguyen et al. |
| 2004/0034351 A1 | 2/2004 | Sherman et al. |
| 2004/0039384 A1 | 2/2004 | Boehm et al. |
| 2004/0059333 A1 | 3/2004 | Carl et al. |
| 2004/0082954 A1 | 4/2004 | Teitelbaum et al. |
| 2004/0082960 A1 | 4/2004 | Davison |
| 2004/0082961 A1 | 4/2004 | Teitelbaum |
| 2004/0087950 A1 | 5/2004 | Teitelbaum |
| 2004/0092934 A1 | 5/2004 | Howland |
| 2004/0093001 A1 | 5/2004 | Hamada |
| 2004/0106934 A1 | 6/2004 | Grossman |
| 2004/0133201 A1 | 7/2004 | Shluzas et al. |
| 2004/0138662 A1 | 7/2004 | Landry et al. |
| 2004/0143265 A1 | 7/2004 | Landry et al. |
| 2004/0143268 A1 | 7/2004 | Falahee |
| 2004/0147928 A1 | 7/2004 | Landry et al. |
| 2004/0147936 A1 | 7/2004 | Rosenberg et al. |
| 2004/0172022 A1 | 9/2004 | Landry et al. |
| 2004/0176763 A1 | 9/2004 | Foley et al. |
| 2004/0194791 A1 | 10/2004 | Sterman et al. |
| 2004/0215190 A1 | 10/2004 | Nguyen et al. |
| 2004/0215193 A1 | 10/2004 | Shaolian et al. |
| 2004/0236317 A1 | 11/2004 | Davison |
| 2004/0254576 A1 | 12/2004 | Dunbar et al. |
| 2004/0260287 A1 | 12/2004 | Ferree |
| 2004/0267279 A1 | 12/2004 | Casutt et al. |
| 2005/0010220 A1 | 1/2005 | Casutt et al. |
| 2005/0010221 A1 | 1/2005 | Dalton |
| 2005/0021030 A1 | 1/2005 | Pagliuca et al. |
| 2005/0021031 A1 | 1/2005 | Foley et al. |
| 2005/0033297 A1 | 2/2005 | Davison |
| 2005/0038432 A1 | 2/2005 | Shaolian et al. |
| 2005/0038434 A1 | 2/2005 | Mathews |
| 2005/0043741 A1 | 2/2005 | Michelson |
| 2005/0043742 A1 | 2/2005 | Bruneau et al. |
| 2005/0059969 A1 | 3/2005 | McKinley |
| 2005/0065515 A1 | 3/2005 | Jahng |
| 2005/0065517 A1* | 3/2005 | Chin .......................... 606/61 |
| 2005/0070917 A1 | 3/2005 | Justis |
| 2005/0080418 A1 | 4/2005 | Simonson et al. |
| 2005/0085813 A1 | 4/2005 | Spitler et al. |
| 2005/0090822 A1 | 4/2005 | DiPoto |
| 2005/0090833 A1 | 4/2005 | DiPoto |
| 2005/0113833 A1 | 5/2005 | Davison |
| 2005/0124991 A1 | 6/2005 | Jahng |
| 2005/0131407 A1 | 6/2005 | Sicvol et al. |
| 2005/0131408 A1 | 6/2005 | Sicvol et al. |
| 2005/0131421 A1 | 6/2005 | Anderson et al. |
| 2005/0131422 A1 | 6/2005 | Anderson et al. |
| 2005/0137461 A1 | 6/2005 | Marchek et al. |
| 2005/0137593 A1 | 6/2005 | Gray et al. |
| 2005/0149022 A1 | 7/2005 | Shaolian et al. |
| 2005/0149035 A1 | 7/2005 | Pimenta et al. |
| 2005/0154389 A1 | 7/2005 | Selover et al. |
| 2005/0171540 A1 | 8/2005 | Lim et al. |
| 2005/0182410 A1 | 8/2005 | Jackson |
| 2005/0192570 A1 | 9/2005 | Jackson |
| 2005/0245928 A1 | 11/2005 | Colleran et al. |
| 2005/0251139 A1 | 11/2005 | Roh |
| 2005/0277934 A1 | 12/2005 | Vardiman |
| 2005/0277942 A1 | 12/2005 | Kullas et al. |
| 2006/0030839 A1 | 2/2006 | Park et al. |
| 2006/0030858 A1 | 2/2006 | Simonson et al. |
| 2006/0030861 A1 | 2/2006 | Simonson et al. |
| 2006/0111713 A1 | 5/2006 | Jackson |
| 2006/0111714 A1 | 5/2006 | Foley |
| 2006/0200135 A1 | 9/2006 | Sherman et al. |
| 2006/0217735 A1 | 9/2006 | MacDonald et al. |
| 2006/0247658 A1* | 11/2006 | Pond et al. ............. 606/104 |
| 2006/0264934 A1 | 11/2006 | Fallin |
| 2006/0264962 A1 | 11/2006 | Chin et al. |
| 2006/0293680 A1 | 12/2006 | Jackson |
| 2007/0043359 A1 | 2/2007 | Altarac et al. |
| 2007/0083210 A1 | 4/2007 | Hestad et al. |
| 2007/0093824 A1* | 4/2007 | Hestad et al. ............ 606/61 |
| 2008/0009864 A1 | 1/2008 | Forton et al. |
| 2009/0216328 A1 | 8/2009 | Birkmeyer et al. |
| 2009/0228056 A1 | 9/2009 | Jackson |
| 2010/0137915 A1 | 6/2010 | Anderson et al. |
| 2010/0331901 A1 | 12/2010 | Iott et al. |
| 2011/0015678 A1 | 1/2011 | Jackson |
| 2011/0077692 A1 | 3/2011 | Jackson |
| 2011/0152940 A1 | 6/2011 | Frigg et al. |
| 2011/0238120 A1 | 9/2011 | Chin |
| 2011/0245884 A9 | 10/2011 | Brumfield et al. |
| 2012/0089191 A1 | 4/2012 | Altarac et al. |
| 2012/0123477 A1 | 5/2012 | Landry et al. |
| 2012/0158070 A1 | 6/2012 | Jackson |
| 2012/0197302 A1 | 8/2012 | Fallin |

FOREIGN PATENT DOCUMENTS

| | | |
|---|---|---|
| DE | 29710979 | 6/1997 |
| DE | 19726754 | 2/1999 |
| DE | 10027988 | 1/2002 |
| EP | 528177 | 2/1993 |
| EP | 611116 | 8/1994 |
| EP | 665731 | 8/1995 |
| EP | 1006888 | 6/2000 |
| EP | 1374786 | 1/2004 |
| EP | 1468652 | 10/2004 |
| EP | 1545355 | 6/2005 |
| JP | 2003-511190 A | 3/2003 |
| JP | 2006-504505 A | 2/2006 |
| SU | 839513 | 6/1981 |
| WO | 9318722 | 9/1993 |
| WO | 9409726 | 5/1994 |
| WO | 9514437 | 6/1995 |
| WO | 9714457 | 4/1997 |
| WO | 9822030 A1 | 5/1998 |
| WO | 9836785 | 8/1998 |
| WO | 0045720 | 8/2000 |
| WO | 0112080 | 2/2001 |
| WO | 0137744 | 5/2001 |
| WO | 0141681 | 6/2001 |
| WO | 0160234 | 8/2001 |
| WO | 0160263 | 8/2001 |
| WO | 0160270 | 8/2001 |
| WO | 0195823 | 12/2001 |
| WO | 03020110 | 3/2003 |
| WO | 03028566 | 4/2003 |
| WO | 03037170 | 5/2003 |
| WO | 03057055 | 7/2003 |
| WO | 03079914 | 10/2003 |
| WO | 03088810 | 10/2003 |
| WO | 03088878 | 10/2003 |
| WO | 2004004584 | 1/2004 |
| WO | 2004017847 | 3/2004 |
| WO | 2004021899 | 3/2004 |
| WO | 2004028382 | 4/2004 |
| WO | 2004/041100 | 5/2004 |
| WO | 2004037070 | 5/2004 |
| WO | 2004037074 | 5/2004 |
| WO | 2004041100 | 5/2004 |
| WO | 2004058045 | 7/2004 |
| WO | 2004080318 | 9/2004 |
| WO | 2005018466 | 3/2005 |
| WO | 2005023123 | 3/2005 |
| WO | 2005032358 | 4/2005 |
| WO | 2005/060534 A | 7/2005 |
| WO | 2005060534 | 7/2005 |
| WO | 2005/072081 A2 | 8/2005 |
| WO | 2005072081 | 8/2005 |

(56) References Cited

FOREIGN PATENT DOCUMENTS

WO   2006/125029   11/2006
WO   2006116662   11/2006

OTHER PUBLICATIONS

Office Action from U.S. Appl. No. 11/202,487, mailed Aug. 5, 2009.
Office Action from Japanese Application No. 2008-55422 dated Sep. 2, 2011.
Leu et al., Percutaneous Fusion of the Lumbar Spine, State of the Art Reviews, vol. 6, No. 3, pp. 593-604, Sep. 1992.
Kambin et al., Anterior Column Support for Failed Fusion, Revision Spine Surgery, pp. 589-600, from 1999.
Kambin, Arthroscopic Lumbar Intervertebral Fusion, Chapter 95, The Adult Spine, vol. 2, pp. 2037-2046, 1997.
Kambin, The Role of Minimally Invasive Surgery in Spinal Disorders, Advance Operative Orthopedics, vol. 3, pp. 147-171, 1995.
Kambin, "Arthroscopic Microdiscectomy", The Journal of Arthroscopy, vol. 8, No. 3, 1992, pp. 287-295.
Kambin et al, "Percutaneous Posterolateral Lumbar Discectomy and Decompression with a 6.9-millimeter cannula", The Journal of Bone and Joint Surgery, Jul. 1991, pp. 822-831.
Kambin, "Posterolateral Percutaneous suction-excision of herniated lumbar intervertebral discs", Clinical Orthopaedics and Related Research. No. 207, Jun. 1988, pp. 37-42.
Kambin, Posterolateral Percutaneous Lumbar Interbody Fusion, Arthroscopic Microdiscectomy, pp. 117-121, 1991.
Kambin, Posterolateral Percutaneous Lumbar Discectomy and Decompression Arthroscopic Microdiscectomy, Section IV. pp. 67-100, 1991.
Kambin, Minimally Invasive Techniques in Spinal Surgery Current Practice, Neurosurgical Focus, wwwspineuniversecom, 16 pages, printed Aug. 24, 2005.
Diapason, Surgical Texchnique Catalog, Diapasan Spinal System, Jan. 2002.

* cited by examiner

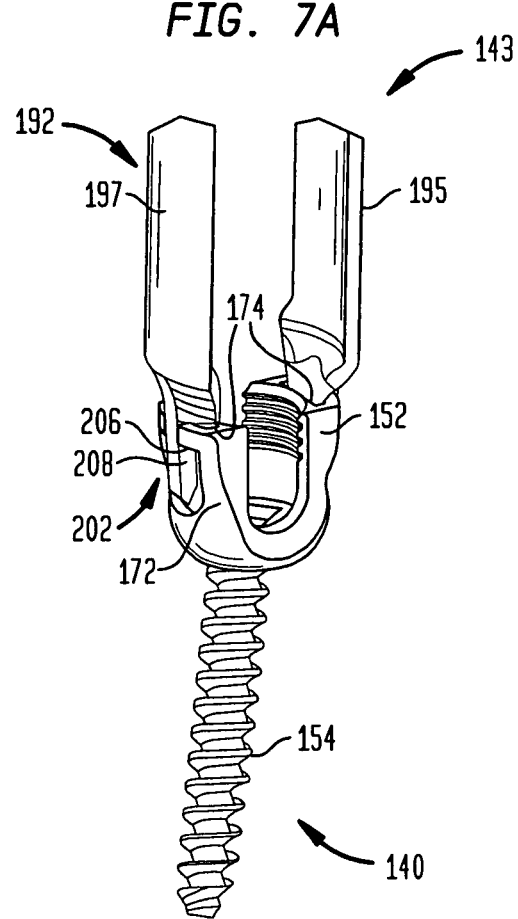

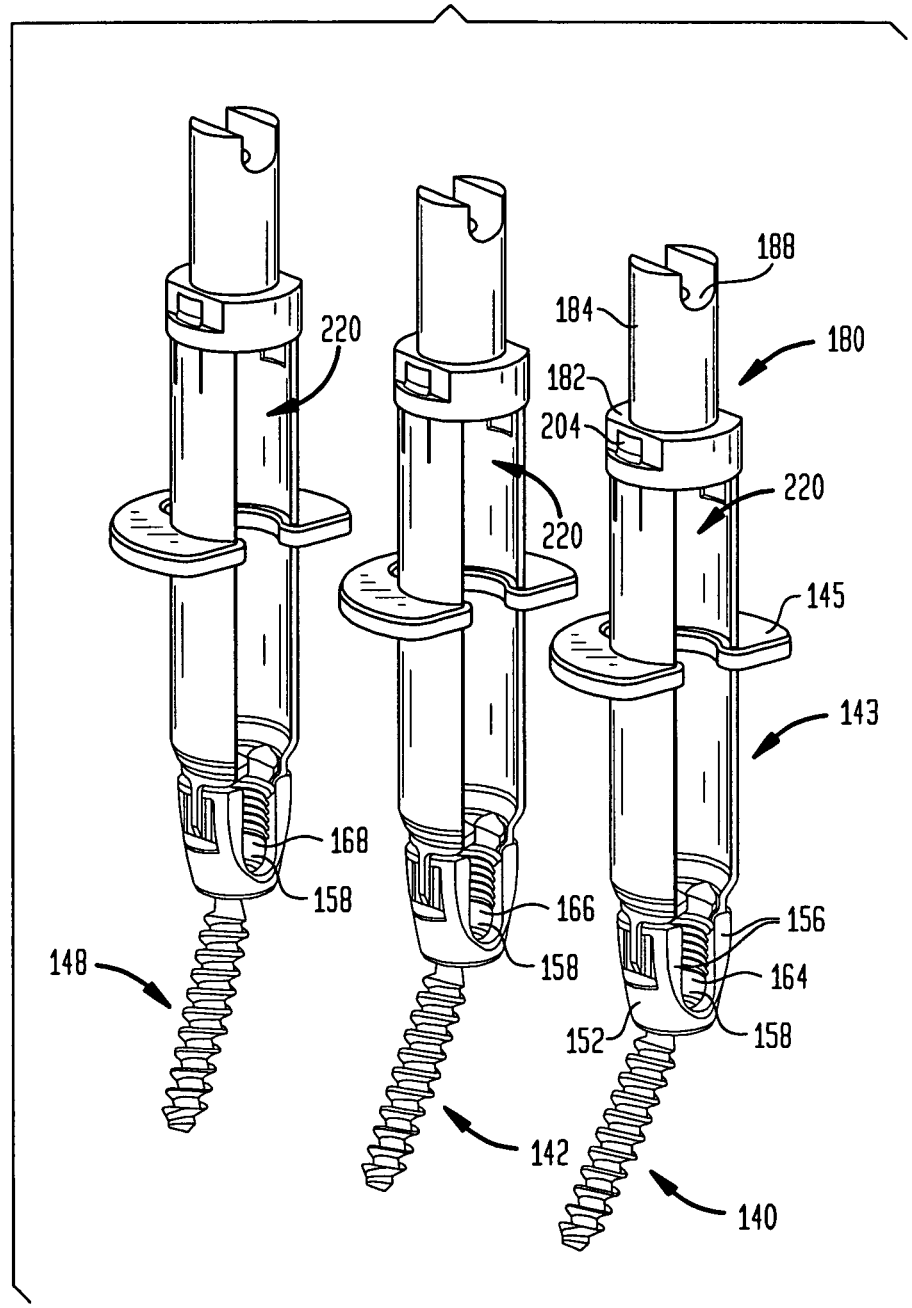

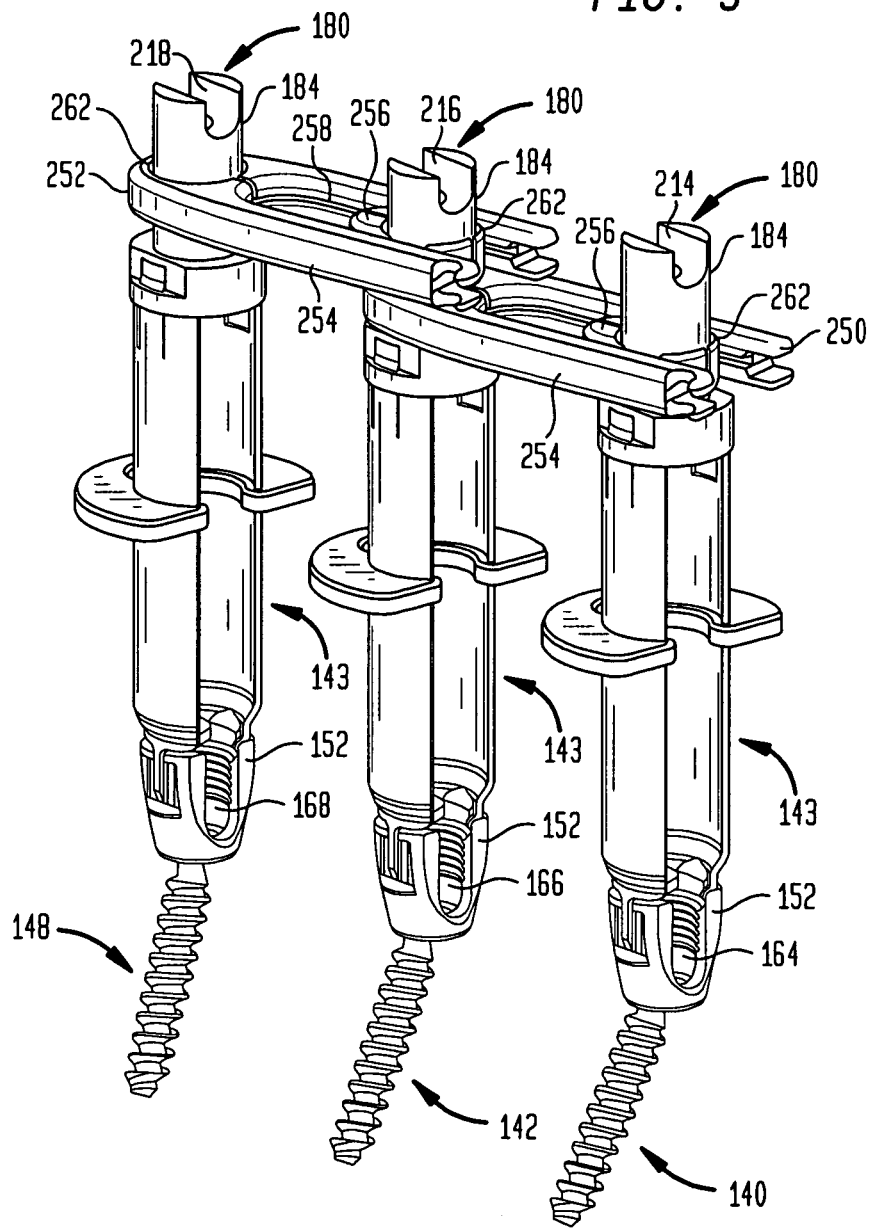

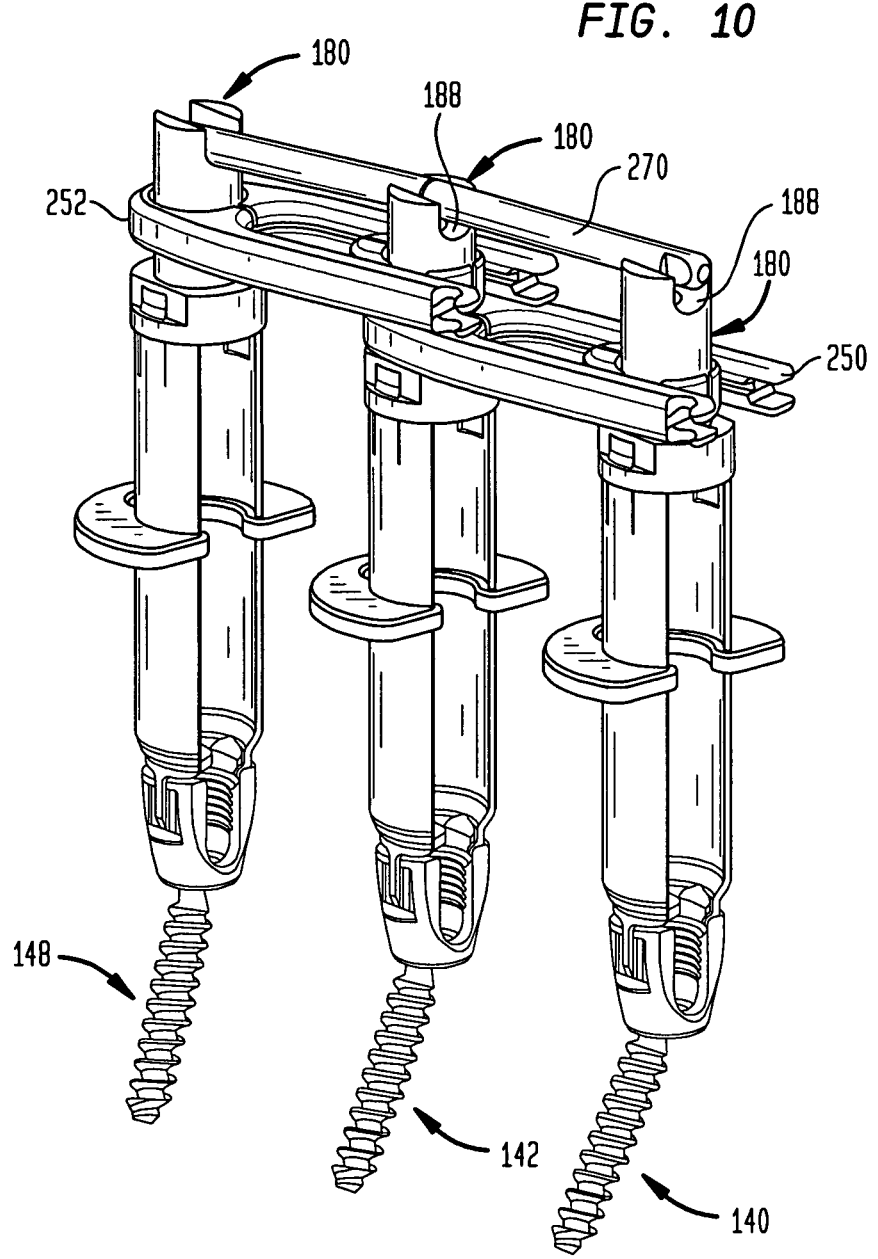

ROD CONTOURING APPARATUS FOR PERCUTANEOUS PEDICLE SCREW EXTENSION

CROSS-REFERENCE TO RELATED APPLICATIONS

This application is a divisional of U.S. application Ser. No. 11/526,785, filed on Sep. 25, 2006, and claims the benefit of the filing date of U.S. Provisional Application No. 60/765,606, filed Feb. 6, 2006, the disclosures of which are hereby incorporated herein by reference.

This application relates to U.S. application Ser. No. 10/868,075, entitled "Methods and Devices For Improving Percutaneous Access In Minimally Invasive Surgeries" and filed on Jun. 15, 2004, U.S. application Ser. No. 11/178,035, entitled "System and Method For Orthopedic Implant Configuration" and filed on Jul. 8, 2005, and U.S. application Ser. No. 11/202,487, entitled "System and Method For Percutaneous Spinal Access" and filed on Aug. 12, 2005, and International Application No. PCT/US2004/036640 and filed on Nov. 4, 2004, the disclosures of which are incorporated herein by reference.

BACKGROUND OF THE INVENTION

The present invention relates to methods and devices for improving percutaneous access in minimally invasive surgeries, and more particularly to methods and devices that provide a template for the extracorporeal selection and contouring of connecting devices based on landmark locations within the body, and the percutaneous transfer of connecting devices and instruments, particularly such selected or contoured devices, within one or more access channels to positions defined by particular locations within the body.

It is well known that traditional surgical procedures in locations deep within a patient's body require a long incision, extensive muscle stripping, prolonged retraction of muscles for visualization, and denervation and devascularization of the adjacent tissue. These procedures result in extensive tissue traumatization and consequently in prolonged recovery time, risk of infections, high hospitalization costs, pain that can be more severe than the pain due to the initial ailment, and in some cases permanent scarring. In minimally invasive surgical procedures, portals are used to access the locations deep in the patient's body. The use of portals rather than a long incision causes less trauma to the adjacent tissue, reduces the recovery time and pain and may be performed in some case under only local anesthesia. The avoidance of general anesthesia reduces post-operative recovery time and the risk of complications.

Minimally invasive surgical procedures are especially desirable for spine surgeries because spine pathologies are located deep within the body without clear muscle planes and there is danger of damaging the adjacent neural and vascular tissues. In treating the majority of spinal pathologies, the spinal muscles are stripped from the bony elements of the spine followed by laminectomy to expose the dura, the nerve roots, and the discs. The incision has to be wide enough and the tissues have to be retracted to maintain a channel from the skin to the floor of the spinal canal that will allow direct visualization. This is similar to an open surgery approach to the knee to expose the menisci versus minimally invasive alternatives such as an arthroscopy which uses 1 centimeter portals under illuminated magnification which results in improved visualization, reduced postoperative knee pain, recovery time, and the destruction of healthy tissue. The destruction to the spinal structures is even more extensive during fusion procedures, which require more lateral tissue dissection and exposure to access the transverse processes and pedicles for placement of pedicle screws, rod constructs for stability, and bone graft under direct vision.

Furthermore, in spine fusion procedures, connecting elements, such as rods, plates or wires are placed and fixed between two or more locations of the spine. Placement of these connecting elements requires open surgery, which is currently one of the major limitations of other percutaneous cannula access methodologies. Accordingly there is a need for inserting and placing these connecting elements between two or more separate spinal locations without performing open surgery.

A wide variety of orthopedic implants exist. Such implants are typically anchored to bones within the body. Every person has different bone structure; accordingly, implants must vary considerably in geometry to meet the needs of a broad range of patients. Connecting elements are an example of an orthopedic implant that often must be specially configured, adjusted, or selected based on the internal anatomical configuration of the patient's bone structure. Although visualization methods such as X-Rays and fluoroscopy can be utilized to help determine bone geometry, contact with the bones must often be made in order to provide a sufficiently accurate measurement of bony landmarks.

Trial fittings of an implant within the body are often required. In open treatment procedures, access to the operation site is typically sufficiently large to allow fitting and adjustment of implants such as connecting devices within the body. This is not feasible in minimally invasive surgical procedures because the surgeon has neither the physical access nor visibility required to test and adjust the device in situ.

According to new minimally invasive surgical (MIS) procedures, many orthopedic implants can be secured to bone through relatively small incisions. Unfortunately, if a larger incision must be made to permit bone measurement and implant selection or configuration, most of the beneficial effects of the MIS implantation procedure will be lost. Accordingly, there is a need in the art for bony landmark measurement and implant selection or configuration methods that can be carried out through small incisions. Such methods should be relatively simple and quick to perform, with comparatively simple instrumentation.

Furthermore, there is a need to provide a system, apparatus and method that solves the combined problems of using minimally invasive surgery for inserting and fastening implants such as connecting elements to bone locations such as spinal vertebrae and also allows configuration of the implants based on internal landmarks locations without performing open surgery.

SUMMARY OF THE INVENTION

In one aspect, the invention features apparatus for use as connectable portals in percutaneous minimally invasive surgery performed within a patient's body. The apparatus includes a first elongated hollow tube having a proximal end and a distal end and defining a first working channel between the proximal end and the distal end when placed within the body cavity and a second working channel transverse to said first working channel comprising two slots along the length of the hollow tube.

In another aspect, the invention features at least a second elongated hollow tube having a proximal end and a distal end and defining a first working channel between the proximal end and the distal end when placed within the body cavity and a second working channel transverse to said first working channel comprising two slots along the length of the hollow tube.

In another aspect of the invention the first and second tubes are sized for delivering carrier devices, surgical instruments, medical devices, fixation devices, vertebral disc replacement devices, interbody devices, fixation tools, connecting devices, connecting tools, tissue, grafting material, or illumination devices, to a pathology location within the body cavity through either the first or second working channels. The surgical instruments may be scissors, scalpels, saws, drills, tissue dilators, biting and grabbing instruments, curettes, knot tying, or cautery. The fixation devices may be screws, hooks, loops, pins, nuts, washers, wires, sutures, or staples. The fixation tools may be screw drivers, pushers, holders, wrenches, staplers, or knot tiers. The connecting devices may be plates, rods, wires, vertebral disc replacements, interbody fusion devices, or articulating versions thereof. The connecting tools may be connecting tools carriers, pushers, screw drivers, and wrenches. The illumination devices may be light sources, fiber optic cables, infrared detectors, magnification devices, and microscopes. The tubes may further comprise a mechanism for engaging and disengaging a fixation device. The tubes may further comprise separable components that can be assembled and disassembled while at least partially within the body.

In an embodiment of the invention the first tube and second tube may comprise appendages at the distal end configured to releasably engage features of the fixation device and secure to the fixation device.

In an aspect of the method of the invention, the first tube comprises a first opening extending the entire width of the first tube and being located in a portion of the first tube within the first body cavity and wherein a cutting tool is used to incise tissue around the first body cavity through the first opening. The method may also include inserting a second elongated hollow tube within a second body cavity of the patient adjacent to the first body cavity, wherein the second tube has a proximal end and a distal end and defining a second working channel between the proximal end and the distal end when placed within the second body cavity. The method also includes incising tissue between the first body cavity and the second body cavity, thereby forming a path extending from the first body cavity to the second body cavity, then inserting a connecting device into or through the first tube and then transferring the connecting device from the first tube to the second tube through the path. The method also includes attaching a first end of the connecting device to a first bone within the first body cavity via a first fixation device and attaching a second end of the connecting device to a second bone within the second body cavity via a second fixation device. The first bone within the first body cavity may be a first vertebra, and the second bone within the second body cavity may be a second vertebra. The first and second fixation devices may be screws, hooks, loops, pins, nuts, washers, wires, sutures, or staples and in a preferred embodiment is a multiaxial pedicle screw. The connecting device may be plates, rods, wires or articulating versions thereof and in a preferred embodiment is a rod. The tissue between the first and the second body cavities may be a lumbodorsal fascia and the path is located either above or below the lumbodorsal fascia. The first and second tubes are sized for delivering carrier devices, surgical instruments, fixation devices, fixation tools, connecting devices, connecting tools, tissue, grafting material, or illumination devices, to a pathology location within the body cavity. The method may also include inserting additional elongated tubes within additional body cavities of the patient adjacent to the first and second body cavities. The method may also include making a second incision on a second location of the patient's skin, then advancing a second guide wire through the second incision, through tissue underlying the second location and into a second underlying bone, then forming the second body cavity around the second guide wire and finally removing the first and second tubes from the first and second body cavities and closing the first and the second incisions.

The present invention has applications in a wide range of surgical procedures, and in particular in spinal procedures such as laminotomy, laminectomy, foramenotomy, facetectomy and discectomy, fusions or disc replacements using an anterior, posterior, postero-lateral, or a lateral approach to the disc space, facet, laminas, pedicles, or transverse processes. The devices and instruments of the present invention have application to surgical techniques that permit each of these several types of surgical procedures to be performed via a single or multiple sequential working channels. The present invention also has application to surgical techniques for preparing a disc space for insertion of an implant into the disc space.

In another aspect, the invention performs a function similar to a surgical navigation system with simple manual instruments that create a mechanical analog of the body target sites outside the body. This invention further provides a convenient template for the shaping of an implantable device to mate with target body sites without requiring a full surgical exposure to access the target body sites. This invention also provides a suitable level of positional control of the template to allow the surgeon discretion in positioning the template and shaping the implantable device.

In a still further aspect the invention provides an apparatus and a method for creating an extracorporeal set of reference features that replicates the spatial positioning of a set of target sites located inside the body, outside of the body. The target sites are preferably anchor sites for an implantable fixation device, but could be preferred locations for delivering therapeutic agents or anatomic locations.

In one embodiment, the invention creates extracorporeal references of the preferred anchor sites within the body for a fixation member to attach to bone anchors applied to the spine. This is accomplished by attaching elongate members to each bone anchors. Typically the members are attached to a first portion of a bone anchor that articulates with respect to a second portion of the bone anchor that is anchored to the bone. In the case of the application of the invention to a spine surgery, the anchors can be a pedicle screw or a pedicle hook for example.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIGS. 7 and 7A are perspective views of guide wires, pedicle screws and an insertion tool as in FIG. 6, with retractor blades having distal ends engaged with the pedicle screws and retained in position by abutment members to form a slotted cannula.

FIG. 8 is a perspective view of the retractor blades, abutment members and pedicle screws of FIG. 7, with trough simulation members used to form assemblies for contouring a fixation member attached to the distal portion of the retractor blades.

FIG. 9 is a perspective view of the assemblies of FIG. 8, with links bridging between the trough simulation members to retain the assemblies in an axially parallel relationship.

FIG. 10 is a perspective view of the cannulas, pedicle screws, trough simulation members, and bridges of FIG. 9, with a fixation member in the form of a rod seated in troughs of the simulation members for contouring.

DETAILED DESCRIPTION

In this application, an "anatomic point" is a location within the body. An anatomic point need not be located on any specific anatomic structure. When applied to anatomy, "proximal" refers to a position relatively closer to the center of the body, and "distal" refers to a position relatively further from the center of the body. However, when referred to a tool or similar implement, "proximal" refers to a portion relatively nearer the operator of the tool or similar implement, and "distal" refers to a portion relatively further from the operator.

The phrase "spatial transformation" refers to any mathematical procedure in which one or more coordinates can be transformed in a manner that permits the original coordinates to be determined based on the results of the transformation. Accordingly, a spatial transformation may involve any combination of translation and rotation of the original coordinates, as long as the transformation can be analytically reversed to permit the original coordinates to be obtained. A "translational spatial transformation" is a spatial transformation in which the original coordinates are all uniformly translated along the same vector.

The term "mate" refers to any type of connection in which cooperating features engage each other to restrict relative motion of the mating parts. The term "couple" is not limited to fixed attachment, but also includes sliding attachment and the like. The term "receive" does not require one item to completely capture another; rather, one item receives another if the first item engages the second item in a manner that restricts relative motion of the items. The term "substantially parallel" means that a range of adjustment is available for limited relative movement of the assemblies, as the surgeon requires, to position the assemblies and also encompasses normal mechanical tolerances and deflections that create variance from geometrically parallel assemblies.

Figure 1:
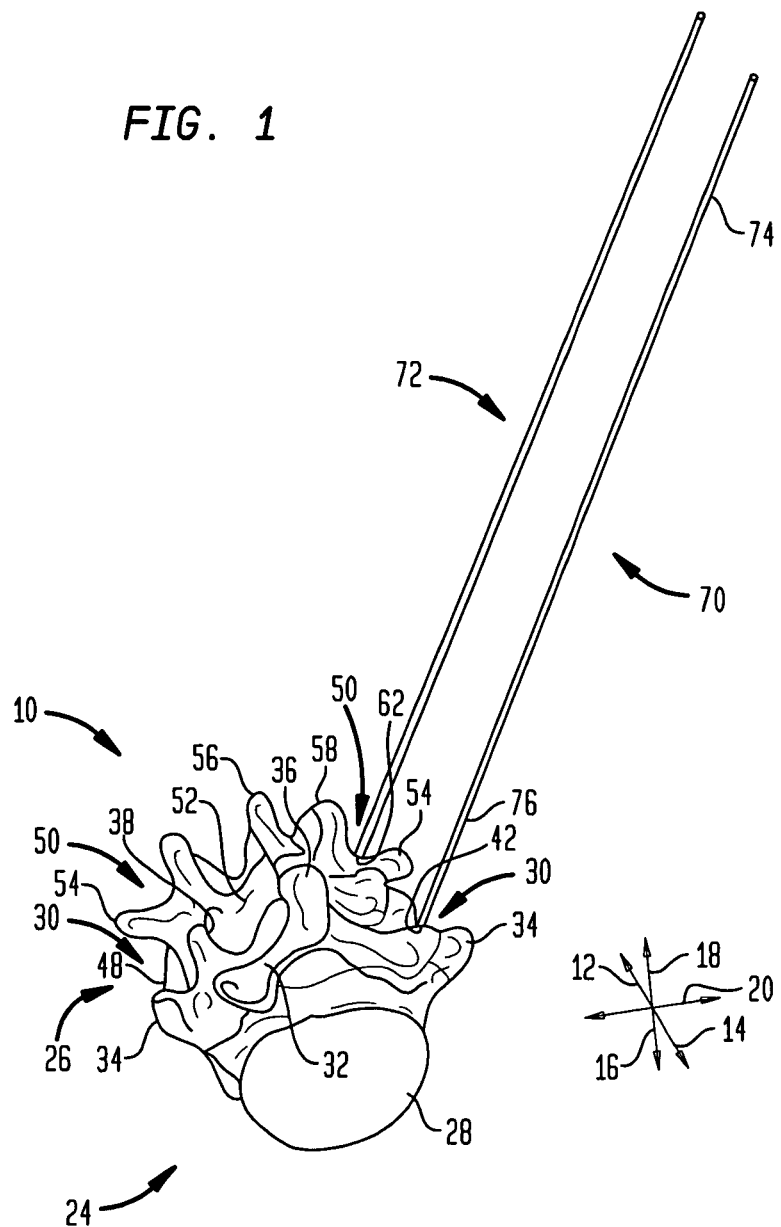
FIG. 1 is a perspective view of two adjacent vertebrae of a spine, with guide wires implanted in the pedicles of the right side.

Referring to FIG. 1, a perspective view illustrates a portion of a spine 10. FIG. 1 illustrates only the bony structures; accordingly, ligaments, cartilage, and other soft tissues are omitted for clarity. The spine 10 has a cephalad direction 12, a caudal direction 14, an anterior direction 16, a posterior direction 18, and a medial/lateral axis 20, all of which are oriented as shown by the arrows bearing the same reference numerals. In this application, "left" and "right" are used with reference to a posterior view, i.e., a view from behind the spine 10. "Medial" refers to a position or orientation toward a sagittal plane (i.e., plane of symmetry that separates left and right sides from each other) of the spine 10, and "lateral" refers to a position or orientation relatively further from the sagittal plane.

As shown, the portion of the spine 10 illustrated in FIG. 1 includes a first vertebra 24, which may be the L5 (Fifth Lumbar) vertebra of a patient, and a second vertebra 26, which may be the L4 (Fourth Lumbar) vertebra of the patient. The systems and methods may be applicable to any vertebra or vertebrae of the spine 10 and/or the sacrum (not shown). In this application, the term "vertebra" may be broadly interpreted to include the sacrum.

As shown, the first vertebra 24 has a body 28 with a generally disc-like shape and two pedicles 30 that extend posteriorly from the body 28. A posterior arch, or lamina 32, extends between the posterior ends of the pedicles 30 to couple the pedicles 30 together. The first vertebra 24 also has a pair of transverse processes 34 that extend laterally from the pedicles 30 generally along the medial/lateral axis 20, and a spinous process 36 that extends from the lamina 32 along the posterior direction 18.

Similarly, the second vertebra 26 has a body 48 from which two pedicles 50 extend posteriorly. A posterior arch, or lamina 52, extends between the posterior ends of the pedicles 50 to couple the pedicles 50 together. The second vertebra 26 also has a pair of transverse processes 54, each of which extends from the corresponding pedicle 50 generally along the medial/lateral axis 20, and a spinous process 56 that extends from the lamina 52 along the posterior direction 18.

The vertebrae 24, 26 and/or the intervertebral disc (not shown) between them, may be damaged or diseased in some manner that makes it desirable to secure the vertebrae 24, 26 together in a manner that prevents relative motion between them. Accordingly, posterior spinal fusion may be employed to secure the pedicles 30 and 50 together in a geometrical relationship that produces a fused spinal section with an appropriate bio-mechanical function. In order to allow the surgeon to provide a proper geometrical relationship between vertebrae, multi-axial pedicle screws and contoured rods connecting the screws have become the gold standard for spinal fusion hardware. FIGS. 1 through 16 illustrate an apparatus and method of configuring and installing a posterior spinal fusion system. FIGS. 17 through 20 illustrate an alternate embodiment for contouring the fixation member.

As further illustrated in FIG. 1, a first guide wire 70 has been inserted into the right-side pedicle 30 of the first vertebra 24, and a second guide wire 72 has been inserted into the right-side pedicle 50 of the second vertebra 26. The guide wires 70, 72 pass through the saddle points 42, 62, respectively, of the pedicles 30, 50. Each of the guide wires 70, 72 has a proximal end 74 and a distal end 76. As shown, the proximal ends 74 are exposed, and the distal ends 76 are implanted in the pedicles 30, 50. The distal ends 76 may be implanted by methods known in the surgical arts.

Figure 2:
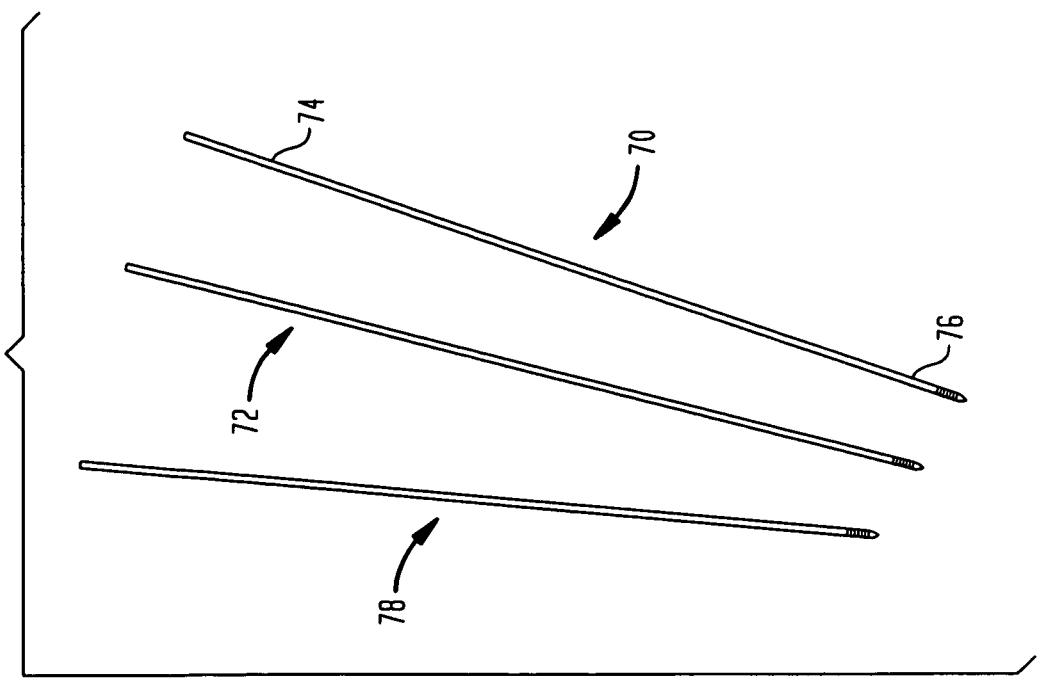
FIG. 2 is a perspective view of three guide wires in isolation, positioned as though implanted in the pedicles of the right sides of three adjacent vertebrae.

Referring to FIG. 2, a perspective view illustrates the first and second guide wires 70, 72 of FIG. 1, with the vertebrae 24, 26 not shown for clarity. The vertebrae are not shown for clarity in the subsequent FIGS. 3-20 also. A third guide wire 78 is also shown. The third guide wire 78 is positioned adjacent to the first and second guide wires 70, 72 as though the third guide wire 78 were implanted in the right-hand pedicle of a vertebra (not shown) directly superior to the second vertebra 26. Accordingly, the method of FIGS. 1 through 20 may be used to secure together vertebrae on multiple levels, not just two adjacent vertebrae.

Figure 3:
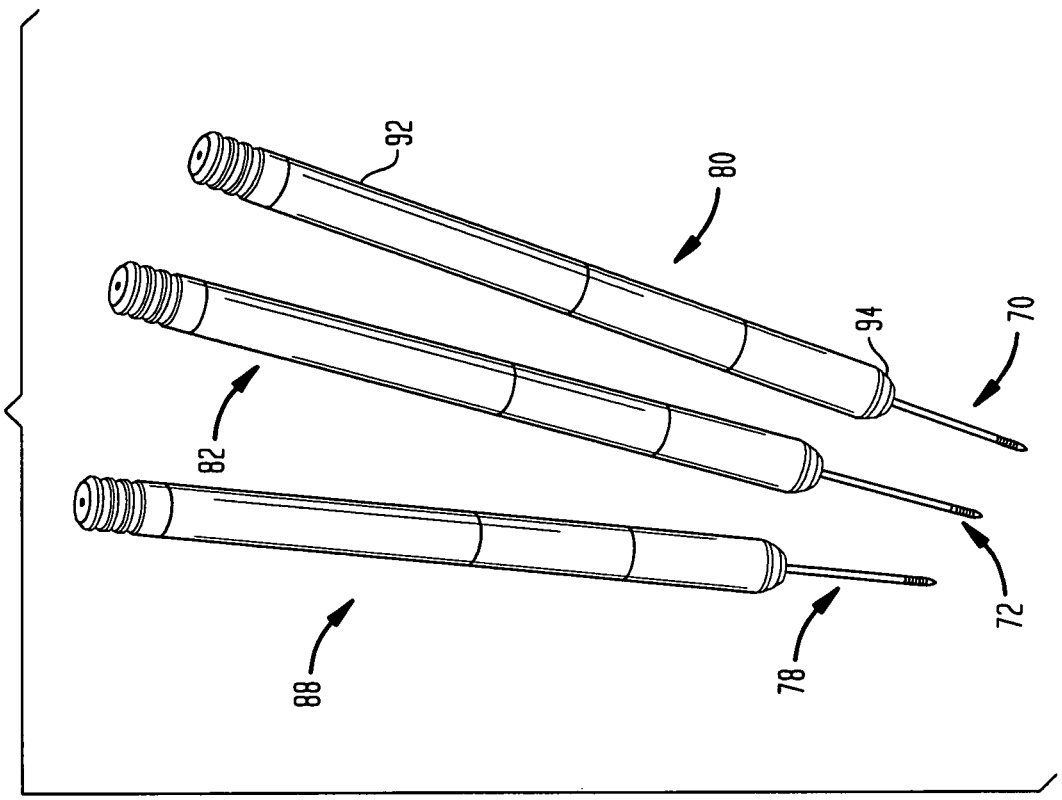
FIG. 3 is a perspective view of the guide wires of FIG. 2, with dilators advanced along the guide wires to dilate surrounding tissue.

Referring to FIG. 3, a perspective view illustrates the guide wires 70, 72, 78, in conjunction with a first dilator 80, a second dilator 82, and a third dilator 88. Each of the dilators 80, 82, 88 has a proximal end 92 and a distal end 94. The proximal ends 92 may be shaped for gripping by hand, or for attachment to a handle or the like. The distal ends 94 are rounded to permit relatively gentle spreading of tissues surrounding the guide wires 70, 72, 78 by the dilators 80, 82, 88.

Each of the dilators 80, 82, 88 has a bore sized to receive the proximal end 74 of the corresponding guide wire 70, 72, or 78, so that the dilators 80, 82, 88 are able to slide along the guide wires 70, 72, 78 toward the distal ends 74, thereby spreading the tissues away from the guide wires 70, 72, 78. As an alternative to the guide wires 70, 72, 78 and the dilators 80, 82, 88, a variety of other guiding devices and/or dilation devices may be used within the scope of the present invention.

Figure 4:
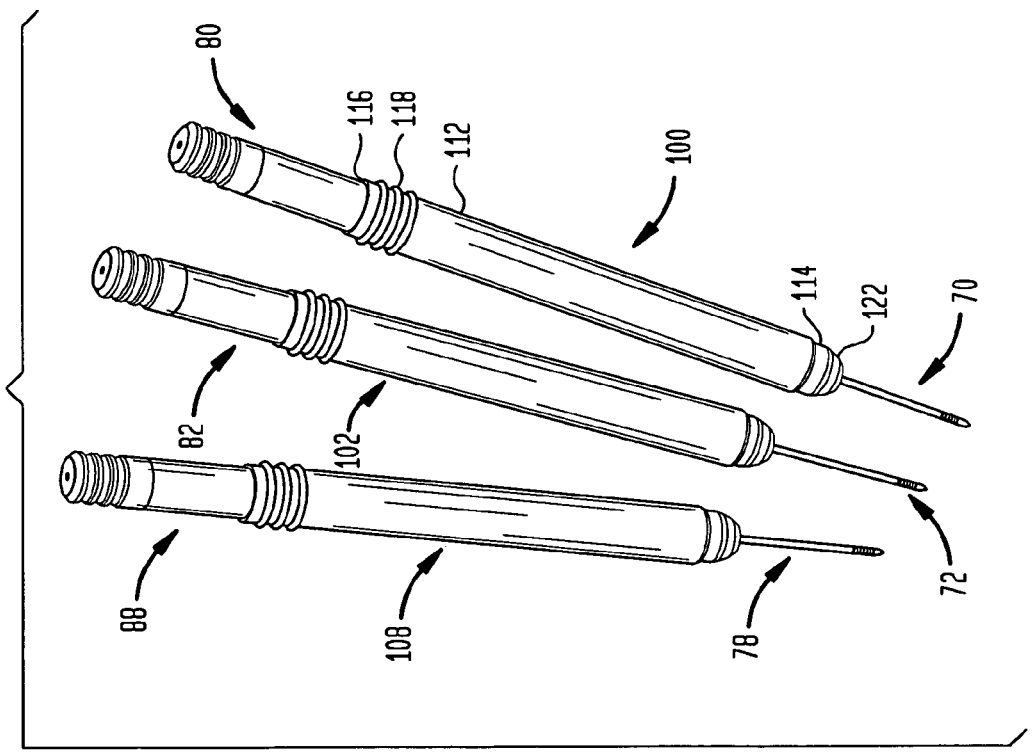
FIG. 4 is a perspective view of the guide wires and dilators of FIG. 3, with cannulas positioned around the dilators.

Referring to FIG. 4, a perspective view illustrates the guide wires 70, 72, 78 and dilators 80, 82, 88, with the addition of a first cannula 100, a second cannula 102, and a third cannula 108. Each of the cannulas 143 has a proximal end 112, a distal end 114, with a bore passing between the proximal and distal ends 112, 114. Each proximal end 112 has a port 116 in communication with the bore, and a tab 118 that may facilitate manipulation or securement of the corresponding cannula 100, 102, or 108.

Each distal end 114 has a taper 122 that provides a reduction in the diameter of the cannula 100, 102, or 108 toward the distal end 114.

The cannulas 143 are inserted around the guide wires 70, 72, 78. The cannulas 143 may be placed by withdrawing dilators 80, 82, 88, inserting the cannulas 143 around the proximal ends 74 of the guide wires 70, 72, 78, inserting the distal ends 94 of the dilators 80, 82, 88 into the ports 116 of the proximal end 112 of the cannulas 143, and then advancing the dilators 80, 82, 88 along the guide wires 70, 72, 78 to urge the cannulas 143 toward the distal ends 76 of the guide wires 70, 72, 78, into the dilated tissue.

According to one alternative method, the dilators 80, 82, 88 are removed to permit placement of the cannulas 143, and are not re-inserted. According to other alternative embodiments, cannulas (not shown) may be modular, or may have dilatable distal ends that enable placement of the cannulas around the dilators 80, 82, 88, so that the dilators 80, 82, 88 need not be removed from the guide wires 70, 72, 78 until the cannulas are properly positioned. The present invention is not limited to use of cannulas like those of FIG. 4; rather, any of a variety of cannulas may be used.

Figure 5:
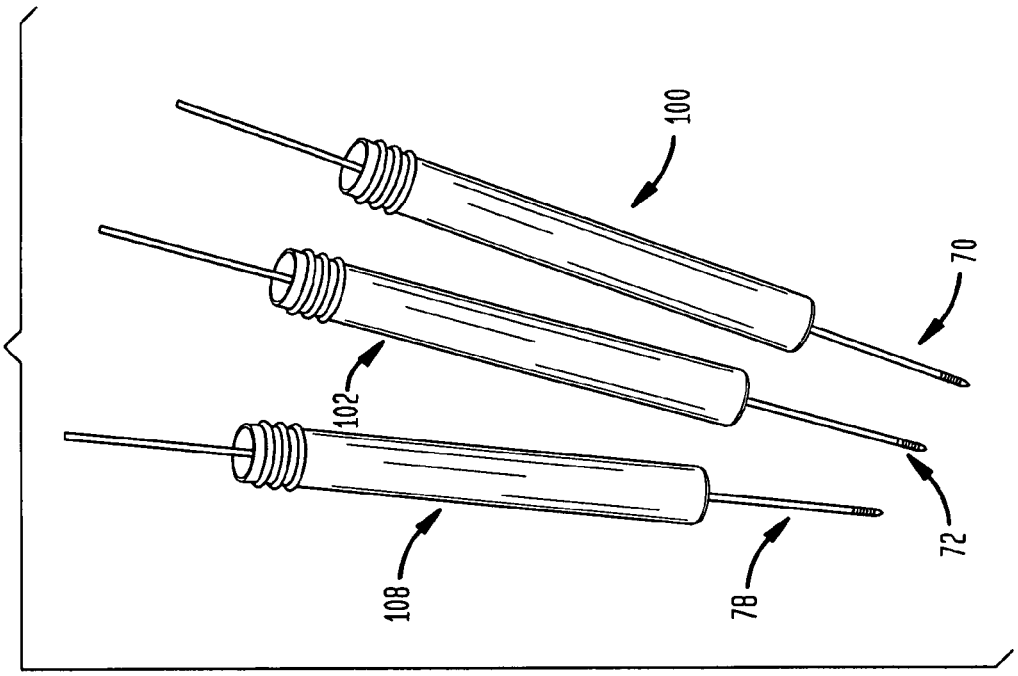
FIG. 5 is a view as in FIG. 4 with the dilators removed.

Referring to FIG. 5, a perspective view illustrates the guide wires 70, 72, 78 and cannulas 143, after the dilators 80, 82, 88 have been removed.

Figure 6:
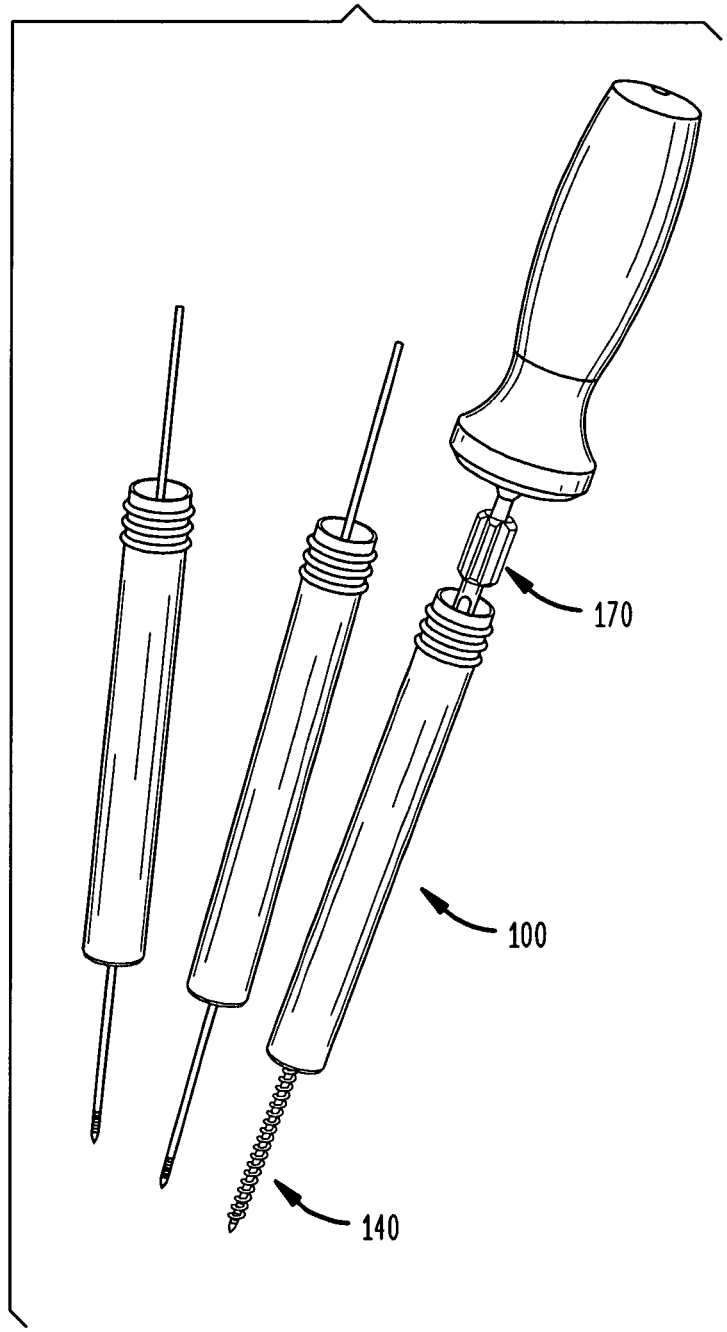
FIG. 6 is a perspective view of the guide wires and cannulas of FIG. 5, with pedicle screws implanted in a pedicle along a guide wire through the use of an insertion tool.

FIG. 6 is a perspective view showing the addition of the first of three cannulated connection elements 140 installed through the cannula 100 and into the vertebra using an insertion tool 170.

Figure 7:
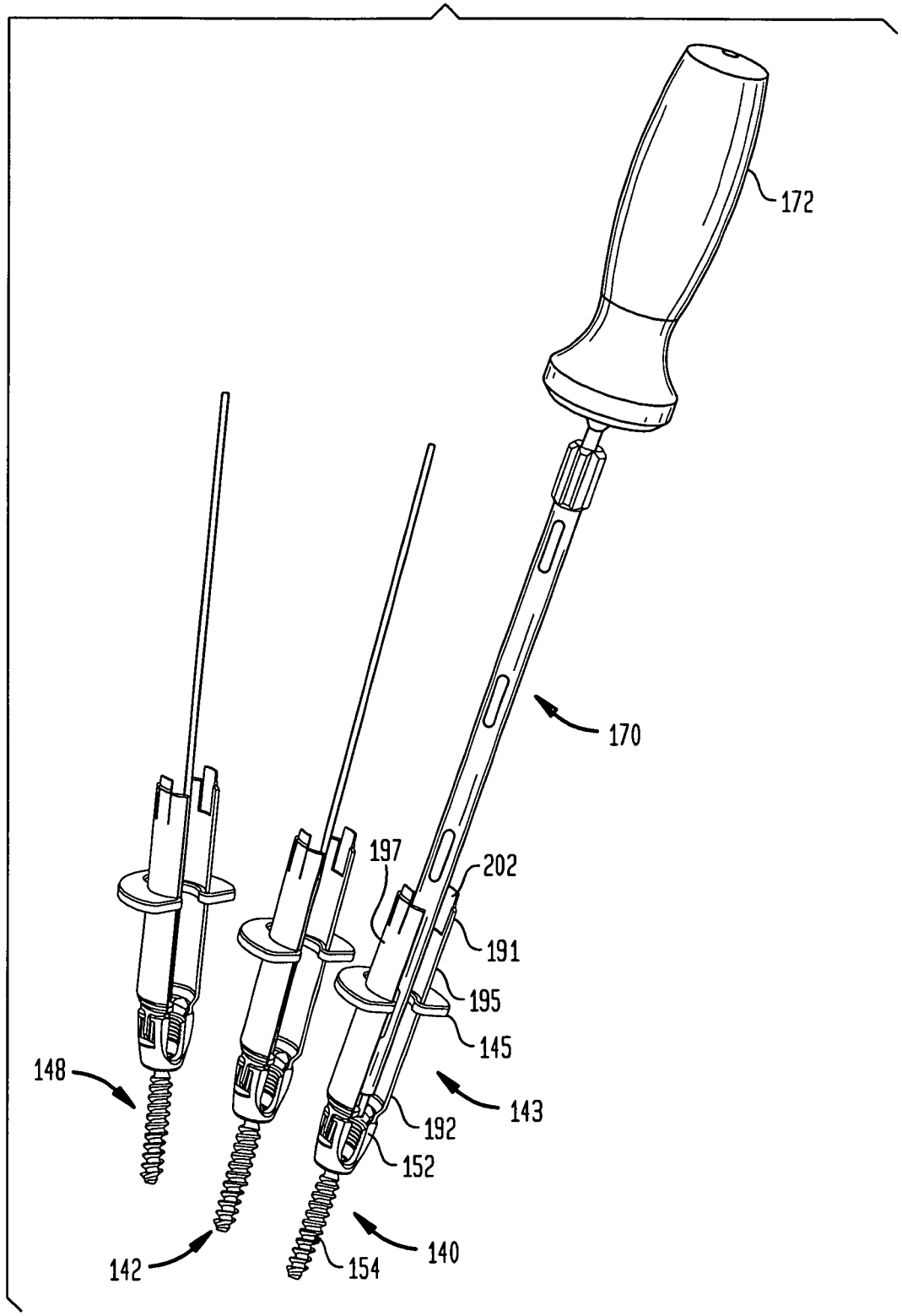

The connection elements may be fixation members designed to anchor a rod to the first vertebra 24, the second vertebra 26, and the third vertebra (not shown in FIG. 6). More precisely, the connection elements may be pedicle screws 140, 142, and 148 implantable in vertebral pedicles, as shown in FIG. 7.

The pedicle screws 140, 142, 148 may be designed to provide poly-axial coupling to the associated pedicles. Each of the pedicle screws 140, 142, 148 has a cage 152 shaped to receive a rod and a screw 154 that passes through an aperture (not visible) of the cage 152 in such a manner that the screw 154 is able to extend from the cage 152 along a plurality of relative orientations. Thus, after the screw 154 has been implanted in a pedicle, the orientation of the cage 152 with respect to the screw 154 can still be altered. Each of the screws 154 has a lumen passing along the axis of the screw 154 so that the screws 154 can slide along the guide wires, 70, 72, 78 for accurate implantation in the pedicles.

As seen in FIG. 8, each cage 152 has two arms 156 that extend generally away from the screw 154 and define a trough 158 through which a rod (not shown in FIG. 5) can pass. The closed end of the trough 158 is rounded in a manner that corresponds to the radius of the rod to be retained within the cage 152 to facilitate secure retention of the rod. The inward-facing surfaces of the arms 156 may be threaded to enable the arms 156 to receive a nut (shown in FIG. 14). Tightening of the nut then presses the rod against the head 154 (shown in FIG. 14) of the screw 154 to keep the rod in place within the slot 158 and to lock the orientation of the screw 154 with respect to the cage 152.

The pedicle screws 140, 142, 148 represent only one of many types of connection elements that may be used in connection with the present invention. A variety of known devices may be used to secure a rod to a plurality of vertebra to provide posterior fusion.

Upon implantation in the pedicles, the pedicle screws 140, 142, 148 are positioned such that a first anatomic point 164, a second anatomic point 166, and a third anatomic point 168 are within the troughs 158 of the cages 152 of the first pedicle screw 140, the second pedicle screw 142, and the third pedicle screw 148, respectively. Upon installation of the rod in the troughs, the axis of the rod is to pass through the anatomic points 164, 166, 168.

Referring back to FIG. 7, seen extending from the connecting element 140, is a slotted cannula 143 and an abutment member 145. The cannula 143 is used to maintain access to the connecting element 140 after it has been implanted in the pedicle in a manner that facilitates percutaneous placement of the rod and attachment of the rod to the connecting element 140. The abutment member 144 helps to hold the cannula 143 together and keep it secured to the connecting element 140 in a manner that will be described subsequently. Additional cannulas 143 can be attached to pedicle screws 142 and 148.

Prior to the installation of the connecting element 140 shown in FIG. 6, the slotted cannula 143 is assembled to the connecting element 140 as visible in FIG. 7. Upon assembly, the cannula 143 will have a proximal end 191 and a distal end 192. The cannula 143 may be dimensioned such that the proximal end 190 protrudes above the skin while the distal end 192 is securable to the cage 152 and is insertable through the skin along with the cage 152. The cannula 143 includes a first retractor blade 195 and a second retractor blade 197, which may be substantially identical to each other. Each of the blades 195, 197 has a proximal end corresponding to the proximal end 191 of the cannula 143, and a distal end corresponding to the distal end 192 of the cannula 143.

The retractor blades are detachably attached to the first portion of the bone anchor as shown in FIGS. 7 and 7A. Each distal end 192 has a distal tab 202, and each proximal end 191 has a proximal tab 204. Each distal tab 202 has a locking ridge 206 that protrudes generally outward, and extends generally circumferentially. Each distal tab 202 is also elongated, with a thin cross section that permits bending toward and away from the axis (not shown) of the cannula. Each proximal tab 204 has bends 208 that cause proximal tab 204 to jut outward, while remaining generally parallel with the remainder of the corresponding blade 195 or 197.

Each of the distal tabs 202 is insertable through the slot 174 of the adjacent arm 172 of the cage 152 when the corresponding blade 195 or 197 is tilted to position the proximal end inward relative to the distal end. Once the distal tabs 202 have passed through the slots 174, rotation of the blades 195 or 197 back to a position generally parallel to each other, and to the axis of the cage 152, causes the distal tabs 202 to engage the edge of the slots 174 such that the bends 208 in the tab 202 are unable to slide back through the slots 174. Thus, the blades 195 and 197 are then in a locked configuration, and cannot be detached from the cage 152. When they are again moved to the unlocked configuration, i.e., tilted to a position with the proximal ends 191 inward, the retractor blades can be unlocked and detached.

As long as the blades 195, 197 remain generally parallel to each other, the distal end 192 of the cannula 143 remains secured to the cage 152. Thus, the distal tabs 202 form a docking element that removably secures the cannula 143 to the connecting element 140. The abutment member 145 serves to keep the blades 195, 197 parallel to each other to keep the cannula 143 in assembled form and to simultaneously keep the cannula 143 secured to the cage 152 by keeping the blades 195, 197 from rotating into the unlocked configuration. When the cannula 143 is secured to the cage 152, the cannula 143 is in its "docked configuration." When the cannula 143 is removed from the cage 152, the cannula 143 is in its "undocked configuration."

As shown, the abutment member 145 is generally disc-shaped with a central opening and an open side that provides access to the central opening. The abutment member 145 also has a pair of arcuate slots that extend around opposing portions of the central opening and are sized to surround the first and second blades 195, 197 and keep the blades generally parallel to each other, and perpendicular to the abutment member 145. Thus, the blades 195, 197 are unable to pivot to the unlocked configuration when the abutment member 145 is installed to create an assembly and the cannula 143 maintains a generally tubular shape.

After the blades 195, 197 have been inserted into the arcuate slots, the abutment member 145 may be positioned at any of a range of positions along the cannula 143. Thus, upon implantation of the pedicle screw 140 in the corresponding pedicle, the abutment member 145 can be positioned abutting the outward-facing surface of the patient's skin through which the cannula 143 passes. The abutment member 144 helps to stabilize the cannula 143 with respect to the tissues it passes through.

Once assembled to the pedicle screw 140, the cannula 143 has slots 220 extending along its entire longitudinal length, along opposite sides of the cannula 143. The slots 220 extend to the cage 152, and are therefore contiguous with the recesses defined in the arms 172 of the cage 152. Upon installation of the cannula and pedicle screw assembly by using the cannula 100 and tool 170 as shown in FIG. 6, the slots 220 will extend along the entire subcutaneous length of the cannula 143 as better seen in FIG. 8. Therefore, the rod for connecting the pedicle screws 14, 142, 148 may be inserted percutaneously through the slots 220 along a direction transverse to the axis of the cannula 143, and may then be moved through the slots 220 along the anterior direction 16, directly into the trough of the cage 152.

The pedicle screws 140, 142, 148, with or without the assembled cannulas 143, may be installed in a variety of ways. According to one method, the dilators 80, 82, 88 are first removed. Then, each of the pedicle screws 140, 142, 148 is implanted through the use of an insertion tool 170. The insertion tool 170 has a handle 172 designed to be gripped by a hand, a distal end extending from the handle 172 and engaging the head of each of the screws 154. Thus, torque applied to the handle can be transmitted to each of the screws 154.

The stem 174 also has a lumen (not shown) sized to fit around each of the guide wires 70, 72, 78 so that the guide wires 70, 72, 78 can be used to guide implantation of the screws 154 through the use of the insertion tool 170. Slots 178 provide access to the lumen for cleaning.

Each of the screws 140, 142, 148 is coupled to the insertion tool 170 by connecting the head 154 of the screws to the distal end 176 of the stem 174. The insertion tool 170 is then moved to insert the proximal end 74 of the corresponding guide wire 70, 72, 78 through the lumen of the screw 154 and into the lumen of the stem 174. The insertion tool 170 is used to insert the pedicle screw 140, 142, or 148 through the corresponding cannula 100, 102, or 108 until the screw 154 contacts the first pedicle 30, the second pedicle 50, or the third pedicle. Then, torque and axial pressure are applied to the tool 170 to embed the threads of the screw 154 into the bone. The same method may be used to implant all three of the pedicle screws 140, 142, 148. After the pedicle screws 140, 142, 148 have been implanted, the guide wires 70, 72, 78 may be removed.

As previously discussed, the fixation member in the form of a rod for connecting the pedicle screws 140, 142, 148 must be configured in three dimensional space to match the geometrical targets 164, 166, 168, in order to allow the pedicle screws to constrain the vertebrae in the desired positions once they are fastened to the rods. This requires that the rod be contoured. For better precision in contouring the fixation member, simulation members, such as the trough simulation members 180 with base 182, stem 184 and troughs 188 as shown in FIG. 8, may be attached to the proximal end 191 of the cannula 143 to better replicate the geometry of the geometrical targets 164, 166, 168. In conjunction with the cannula 143, the trough simulation members 180 provide a translational spatial transformation of the troughs 158 of the pedicle screws to the troughs 188 in order to use the troughs 188 as an extracorporeal template to bend the rod. The rod will later be attached in the troughs 158 of the pedicle screws 140, 142, 148 attached to the vertebrae within the body of the patient, placing the central axis of the rod in the troughs 158 to match the geometrical targets 164, 166, 168 at each trough location.

As shown in FIG. 8, the particular attachment method employed for the trough simulation members 180 attaches the member to each proximal cannula end 191 with a proximal tab 204 releasably engaged with a slot in the trough simulation member. As will be later described, the trough simulation members 180 are but one example of a simulation member and other arrangements that project the positional relationship of the troughs 158 outside the body to achieve a translational spatial transformation, such as rods or cannulas that locate on the troughs 158 directly rather than through a cannula 143 are within the scope of the inventions. Regardless of the configuration of the simulation members, the members must be retained in an approximately parallel axial relationship, be of the same length, and maintain the same alignment of each set of troughs 158 and 188 when using the externally projected troughs 188 to gauge the contouring of the rod in order to provide an accurate translational spatial transformation of the troughs 158 and consequently allow the axis of the contoured rod to correctly fit within the troughs 158 in the geometrical targets 164, 166, 168.

Referring to FIG. 9, a perspective view illustrates the cannulas 143, pedicle screws 140, 142, 148, and the trough simulation members 180 of FIG. 8, with the addition of a first link or bridge 250 and a second link or bridge 252. The bridges 250, 252 are used to keep the trough simulation members 180 substantially parallel to each other to constrain the spatial transformation of the anatomic points 164, 166, 168. The bridges 250, 252 are designed to constrain the trough simulation members 180 only to parallelism. Thus, the bridges 250, 252 do not limit relative translation or relative axial rotation of the trough simulation members 180.

Each of the first and second bridges 250, 252 has a first slider 254 and a second slider 256. The first slider 254 of each of the bridges 250, 252 has a pair of grooves 258 that face inward. The second slider 256 of each of the bridges 250, 252 has a pair of flanges that extend outward into the grooves 258 of the corresponding first slider 254 so that the first and second sliders 254, 256 are linearly slidable relative to each other to permit lengthening or shortening of the bridges 250, 252. Each of the sliders 254, 256 also has an aperture 262 that fits around the stem 184 of the corresponding trough simulation members 180. The apertures 262 are sized to fit around the stems 184 with relatively little clearance so that the bridges 250, 252 keep the trough simulation members 180 and thus the attached cannulas 143 and cages 152 parallel to each other without restricting relative axial rotation between the stems 184 and the apertures 162.

The bridges 250, 252 embody only one of many possible configurations that may be used in connection with the invention. According to one alternative embodiment (not shown), each bridge does not have two sliders, but has two members that are rotatably coupled to each other. Each of the members has an aperture like the apertures 262 of the bridges 250, 252, so that the bridges can permit relatively free relative translation and axial rotation of the trough simulation members 180, while keeping the trough simulation members 180 parallel to each other. The bridges would simply elongate and contract through the use of rotary motion instead of linear motion.

Returning to the configuration of FIG. 9, once the bridges 250, 252 have been applied, the trough simulation members 180 axially are parallel. The projected points 214, 216, 218 then mimic the relative positioning of the anatomic points 164, 166, 168 within the body and each pair of real and simulation troughs corresponding to the anatomic and projected points is in the same relative orientation to achieve a translational spatial transformation. Thus, the trough simulation members 180, in conjunction with the cannulas 143 and cages 152, apply a translational spatial transformation to the anatomic points 164, 166, 168 to move them to a more accessible location without altering their positions relative to each other. Accordingly, a rod contoured such that its axis passes through the projected points 214, 216, 218 may be installed such that its axis passes through the anatomic points 164, 166, 168 to properly extend through the cages 152 of the pedicle screws 140, 142, 148. An aspect of the invention is that in order for the projected points 214, 216, 218 to accurately correspond with the relative positioning of the anatomic points 164, 166, 168 within the body, the various mechanical interfaces of the intervening components between the points, such as the trough simulation members 180, the cannulas 143 and the cages 152, must have mechanical interfaces with suitable tolerances, such as axial concentricity and fit, to provide the necessary accuracy.

Referring to FIG. 10, a perspective view illustrates the cannulas 143, the pedicle screws 140, 142, 148, the trough simulation members 180, and the bridges 250, 252 of FIG. 9, with a rod 270 seated in the trough 180 of the trough simulation members 180 for contouring.

Due to natural variations in spinal morphology, the troughs 158 of the pedicle screws 140, 142, 148 may not be arranged in a straight line. Thus, the simulation troughs 180 may not be arranged in a straight line. Consequently, the rod 270 may need to be bent into the proper shape, for example, through the use of tooling such as pliers, French benders, a vice, or the like, so that it will lie properly within simulation trough 180. The process of deforming the rod 270 to the required shape may be termed "contouring."

Contouring may be carried out by, first, placing the undeformed rod 270 in the troughs 180 to determine how the rod 270 should be deformed to lie properly within the troughs 180. Then, the rod 270 is deformed, and again placed in the troughs 180 to check the fit. This process is repeated until the rod 270 is shaped to provide an optimal fit with the troughs 180.

In the alternative to contouring, the rod 270 may simply be selected from a kit or the like. For example, such a kit (not shown) may include rods bent at a variety of angles. The troughs 180 could be used to select the proper rod from the kit by placing each rod, in turn, on the troughs 180 until one is identified that has the proper fit. As another alternative, the rod 270 may be custom fabricated, for example, by measuring the relative positions of the troughs 180 and using a CNC procedure to form the rod 270.

Figure 11:
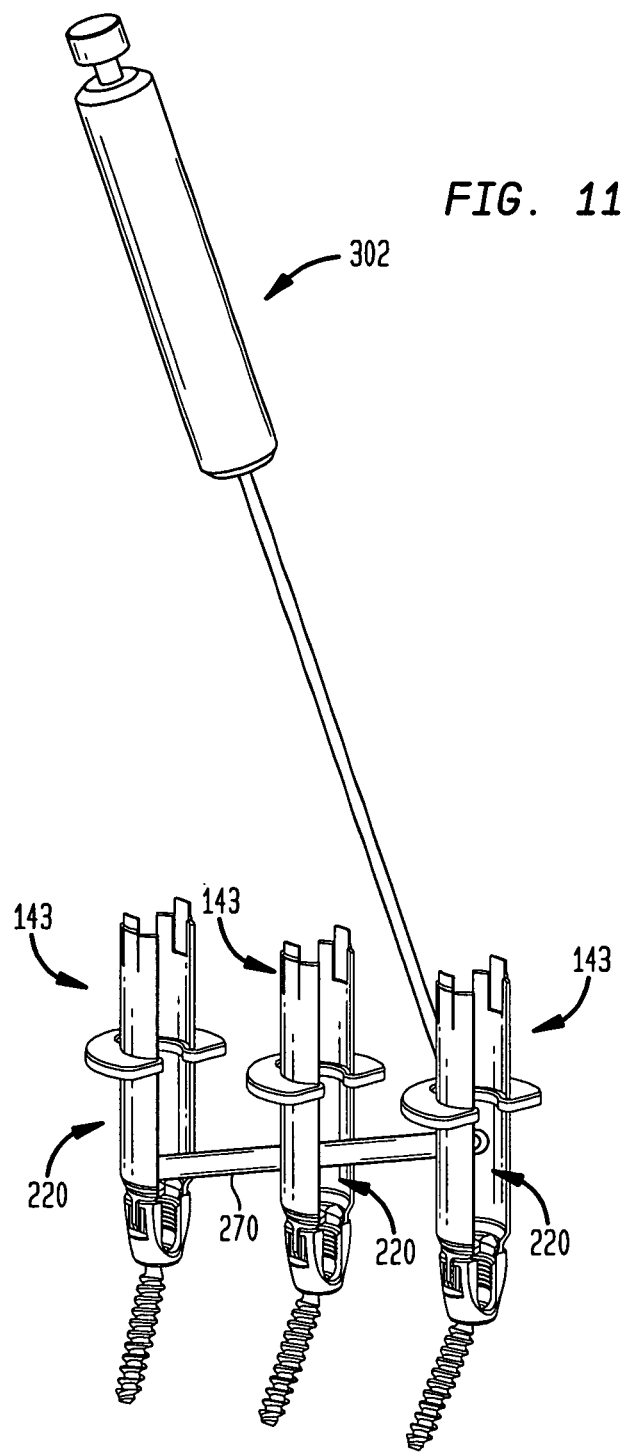
FIG. 11 shows the contoured rod being percutaneously guided through the retractor blades toward the pedicle screws.

After the rod 270 has been configured or selected, the rod 270 and the trough simulation members 180 may be removed from the operating site as shown in FIG. 11, leaving the pedicle screws 140, 142, 148 in place. The cannulas 143 may also be removed at this stage, depending on the method that will be used to implant the rod 270. The rod 270 may be inserted subcutaneously and placed on the cages 152 by making additional incisions to connect the access passageways provided by the cannulas 143. Alternatively, MIS (Minimally Invasive Surgical) techniques, as subsequently described, may be used to implant the rod 270 without making additional major incisions, for example, by inserting the rod 270 subcutaneously and subfascially through the slots 220 of the cannulas 143 using a rod holding tool 302.

Figure 12:
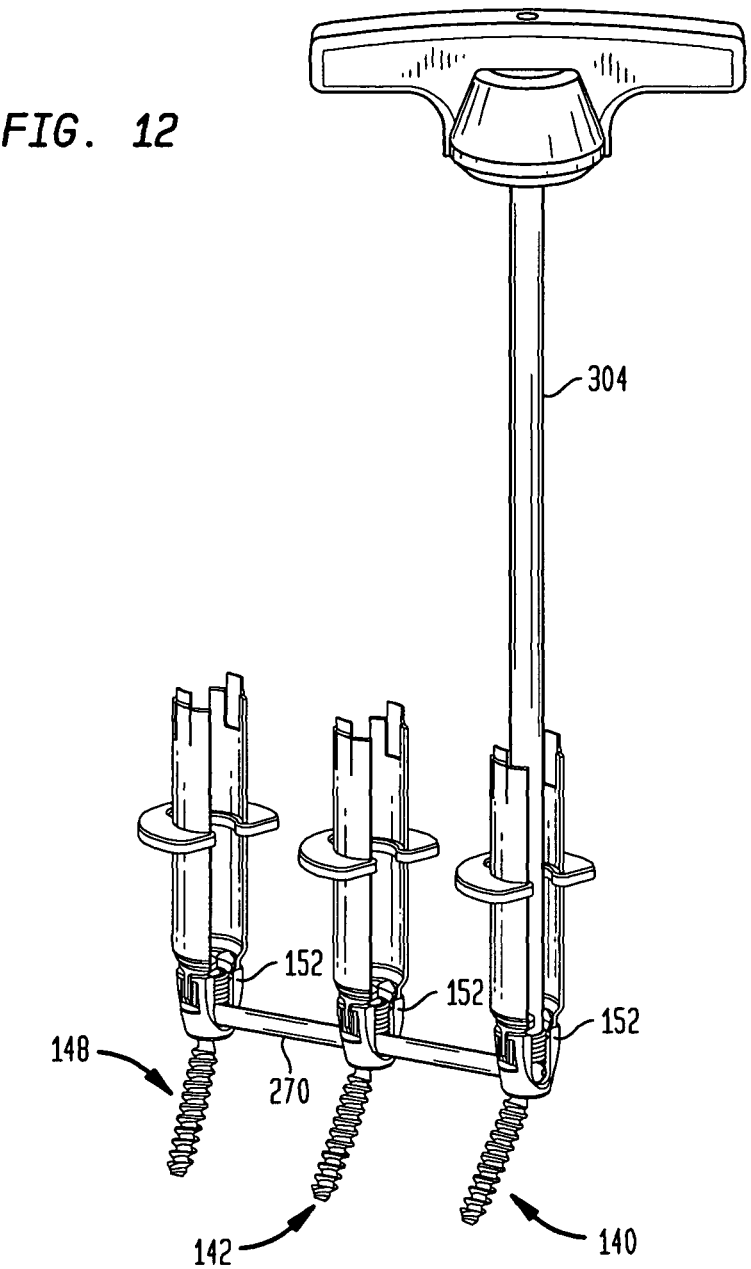
FIG. 12 is a perspective view of the contoured rod, seated in the pedicle screws and being fastened by bolts using a driving tool.
Figure 13:
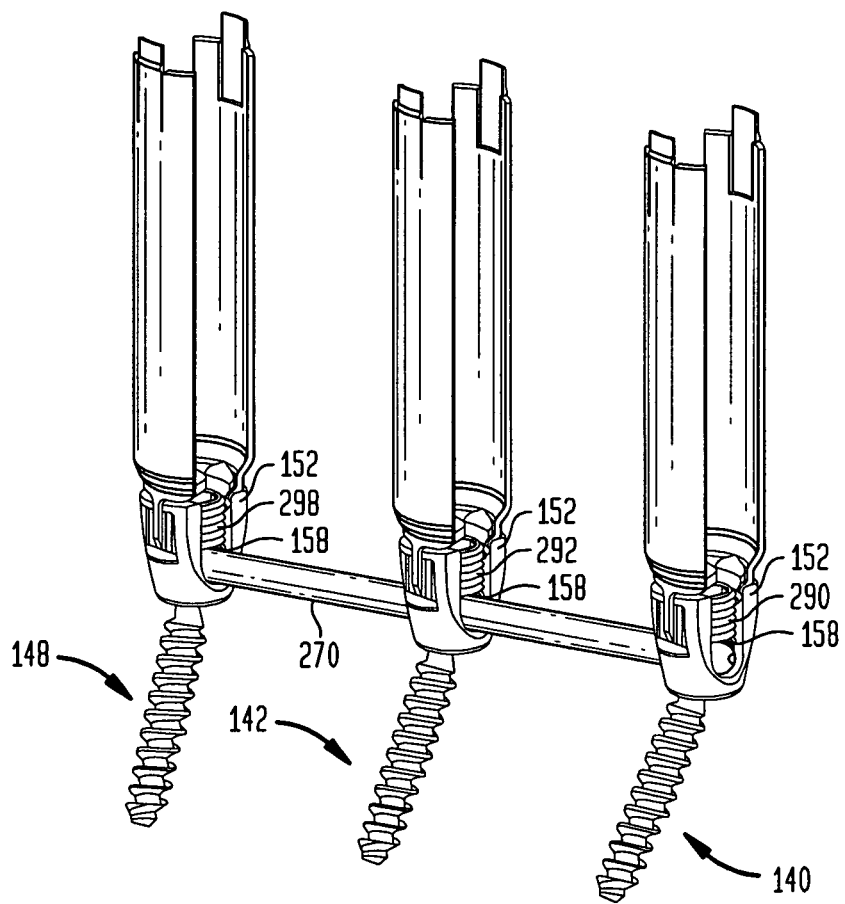
FIG. 13 is a perspective view as in FIG. 14 of the contoured rod fastened to the pedicle screws.
Figure 14:
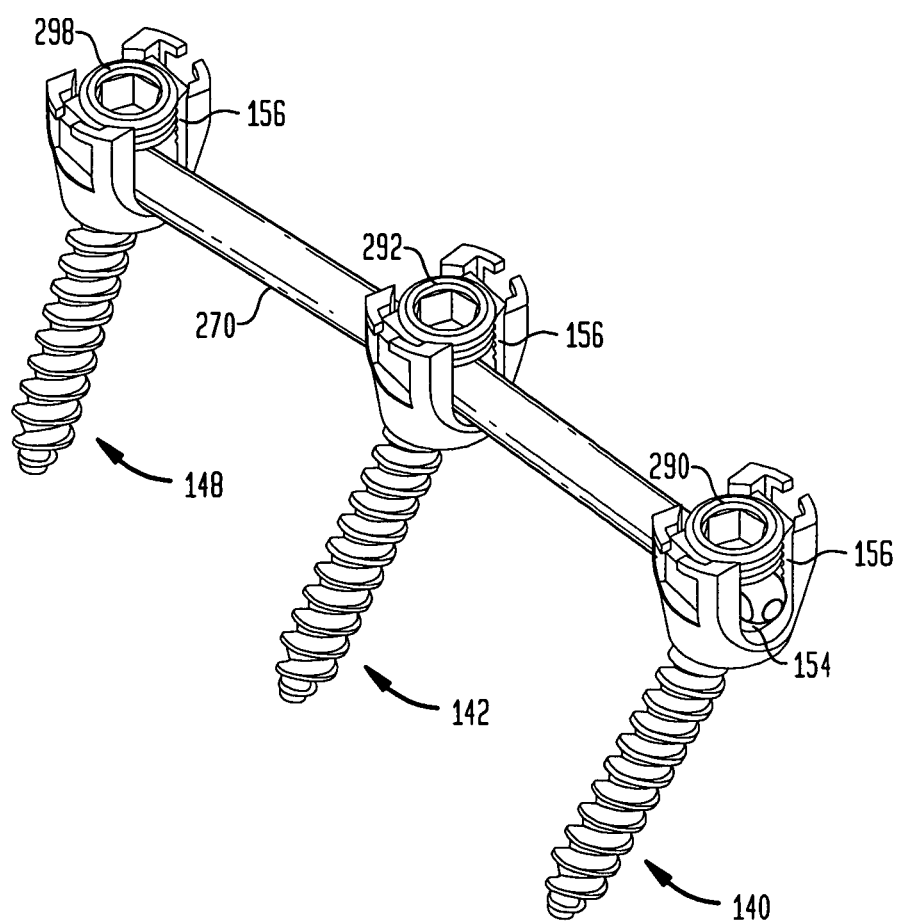
FIG. 14 is a perspective view as in FIG. 15 of the contoured rod fastened to the pedicle screws after removal of the retractor blades.

As shown in FIGS. 12, 13 and 14, the rod 270 has now been seated in the troughs 158 of the cages 152 such that its axis passes through the anatomic points 164, 166, 168. The use of a persuasion tool to seat a rod in a pedicle screw trough is well known in the art. Nuts 290, 292, 298 have been rotated into engagement with the inward-facing surfaces of the arms 156 of the cages 152 of the first, second, and third pedicle screws 140, 142, 148, respectively. The nuts 290, 292, 298 have been tightened with a tool 304 to press the rod 270 against the heads of the heads 154 of the pedicle screws 140, 142, 148, respectively. Thus, the cages 152 are no longer freely rotatable with respect to the screws 154, but are instead locked in their current orientations.

The pedicle screws 140, 142, 148 thus cooperate with the rod 270 to restrict relative motion of the vertebrae to form a posterior vertebral fusion system. If desired, a similar system may be implanted in the left-side pedicles through the method set forth previously to provide a bilateral system. Additionally, the present invention is not limited to a three-level fusion system, but may be used to fuse any number of vertebrae together. To fuse more than three vertebrae together, the steps set forth above may simply be repeated for each additional vertebra, and the rod may be placed on four or more rod interfaces for configuration or selection.

The foregoing is only one of many methods encompassed within the scope of the present invention. According to one alternative method, the trough simulation members 180 may be omitted entirely from the procedure. Such a method may commence with the steps outlined above in the descriptions of FIGS. 1 through 7, but may then include the steps illustrated in FIGS. 15 and 16.

Figure 15:
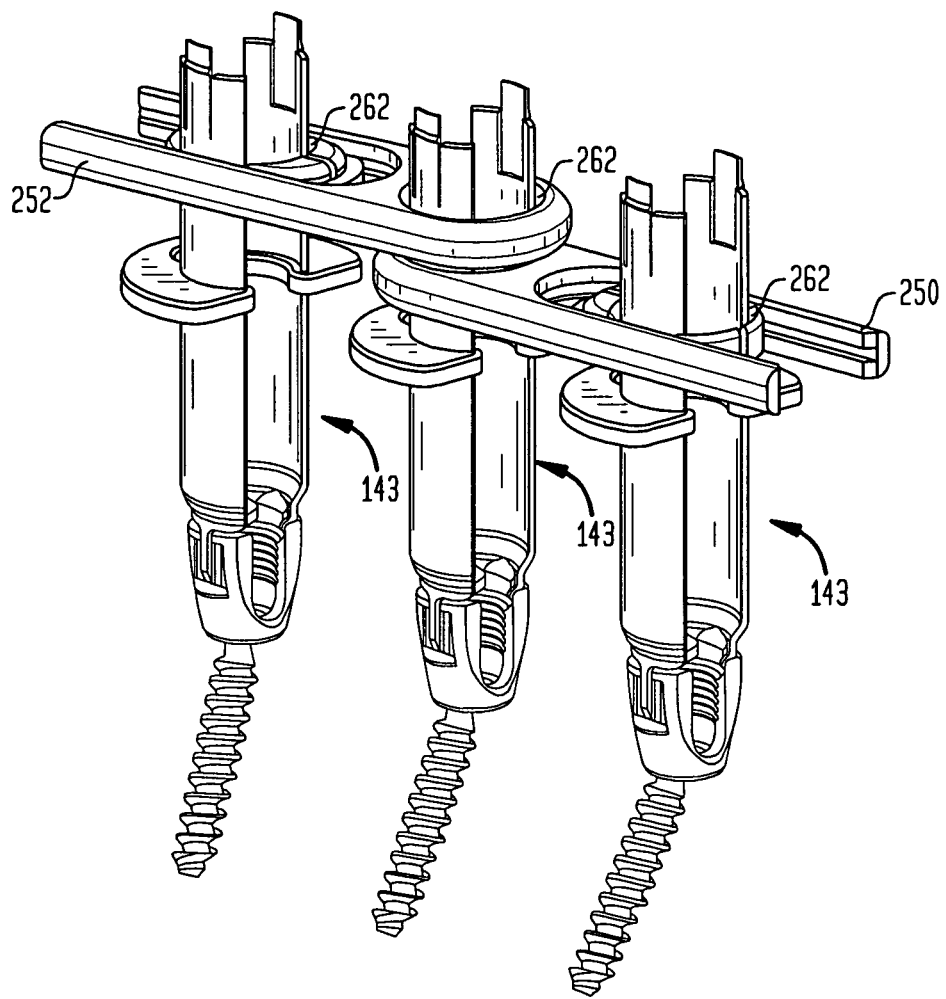
FIG. 15 is a perspective view as in FIG. 9 except that the trough simulation members are not used and the links engage the retractor blades to retain the assemblies in an axially parallel relationship.
Figure 16:
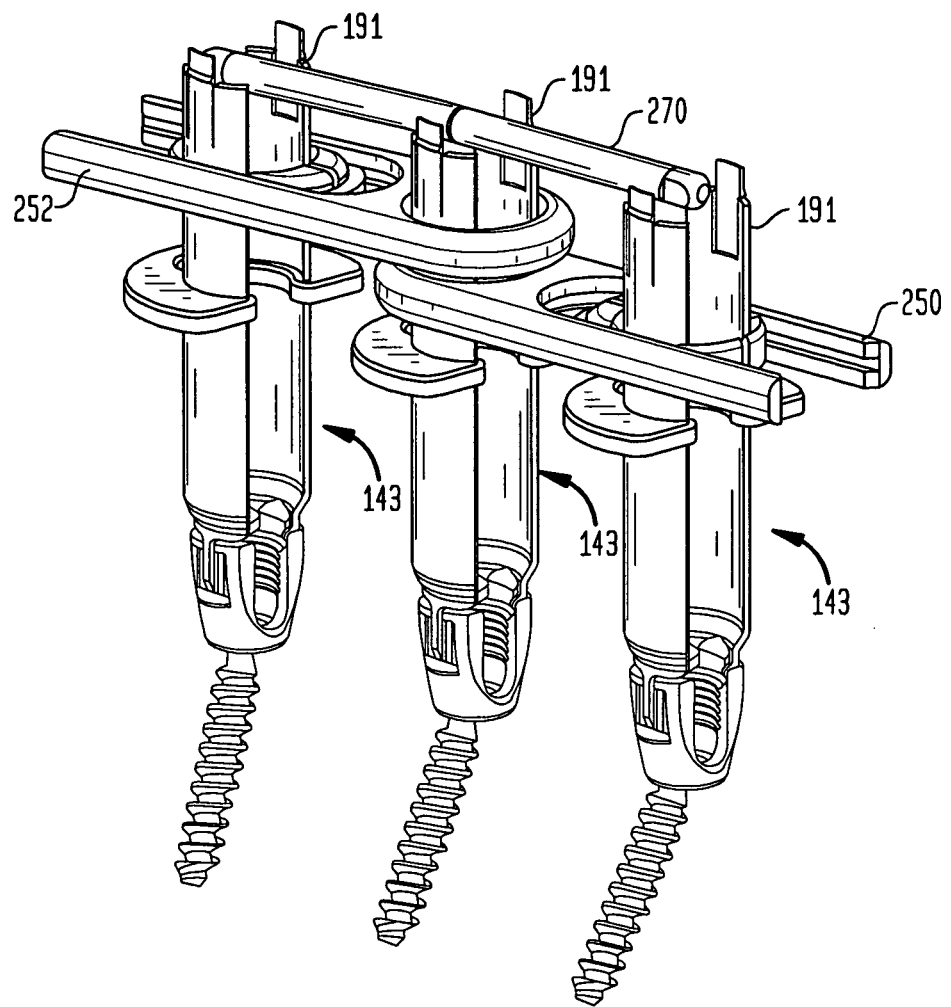
FIG. 16 is a perspective view as in FIG. 10 showing that the distal portion of the retractor blades may be used in place of the troughs for contouring the rod.

Referring to FIGS. 15 and 16, a perspective view illustrates that in this embodiment the apertures 262 of the bridges 250, 252 are sized to fit in close sliding contact with the outer surfaces of the cannulas 143 in order to keep the cannulas parallel to each other. The rod 270 is then manually positioned at the proximal end 191 of the cannula 170 and visually evaluated to conduct the contouring or selection process described in conjunction with FIG. 10. While not providing the accuracy of an embodiment using simulation members, this method may be used to shorten the time necessary for the contouring step or be may be used to contour a trial rod or may be used for an initial contouring of a rod before using a simulation member.

Figure 17:
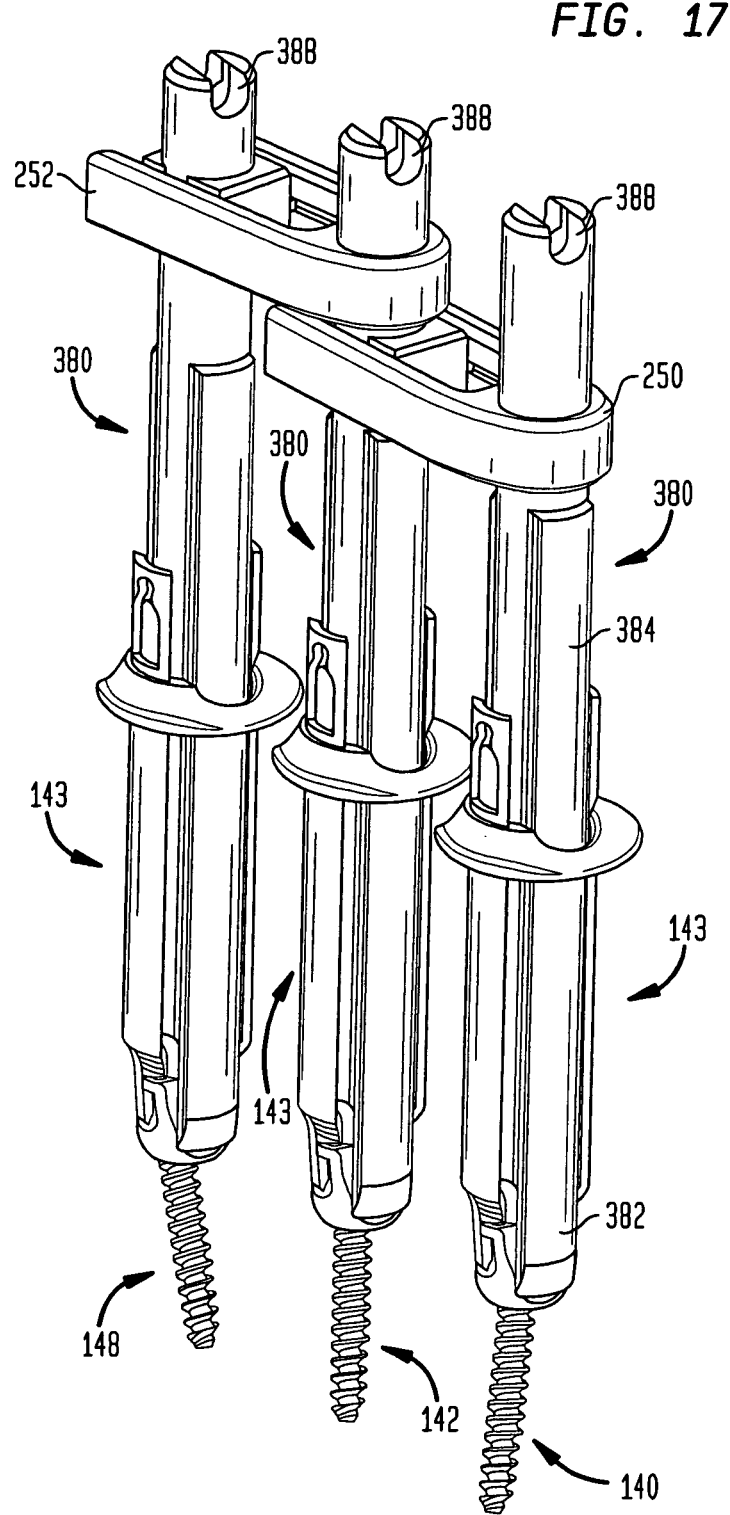
FIG. 17 is a perspective view of the assemblies as in FIG. 8, with extenders that replace the trough simulation members and pass through the slotted cannulas to provide a contouring feature.
Figure 18:
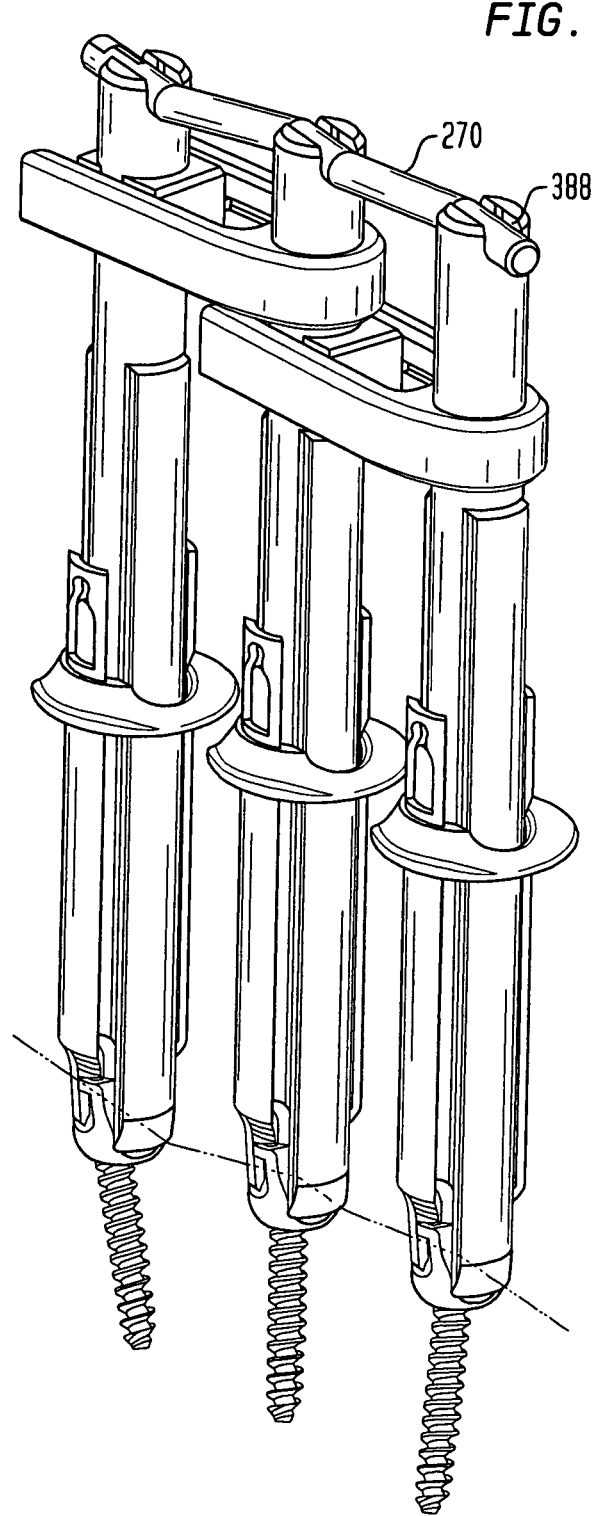
FIG. 18 is a perspective view of the cannulas, pedicle screws, extenders, and bridges of FIG. 17, with a fixation member in the form of a rod seated in troughs of the simulation members for contouring.

FIGS. 17 through 20 depict an embodiment that uses a different type of simulation member than the trough simulation members 180 discussed above. As seen in FIG. 17 trough simulation rods 380 project the positional relationship of the troughs 158 outside the body, by passing through cannulas 143 and locating directly on the troughs 158. The trough simulation rod 380 has a trough interface 382, an elongate shaft 384 and simulation troughs 388 located at the proximal end of the rod. The trough interface 382 is configured to locate on the troughs 158 of the pedicle screws 140,142,148 attached to the vertebrae within the body of the patient, in order to determine the position of the geometrical targets 164, 166, 168 for the central axis of the rod 270. The shaft 384 projects the location of the troughs 158 to simulation troughs 388 external to the body and maintains a close concentric fit with the cannula 143 to ensure an accurate projection. Thus, similar to the previous embodiment using the trough simulation members 180, the trough simulation rods 380 provide a spatial transformation of the troughs 158 of the pedicle screws to the simulation troughs 388 in order to use the troughs 388 as an extracorporeal template to bend the rod. As in the previous embodiment, the trough simulation rods 380 must be retained in an approximately parallel axial relationship by structures such as bridges 250, 252, be of the same length, and maintain the same alignment of each set of troughs 158 and 388 when using the externally projected troughs 388 to gauge the contouring of the rod in order to provide an accurate projection of the troughs 158 and consequently allow the axis of the contoured rod to correctly fit with the troughs 158 in the geometrical targets 164, 166, 168 as previously described. The rod 270 will later be placed in the body and be attached to the pedicle screws as previously described in connection with FIGS. 11-14 and pictured in FIGS. 18-20. In the latter series of figures, a three dimensionally contoured rod 270 is depicted.

Figure 19:
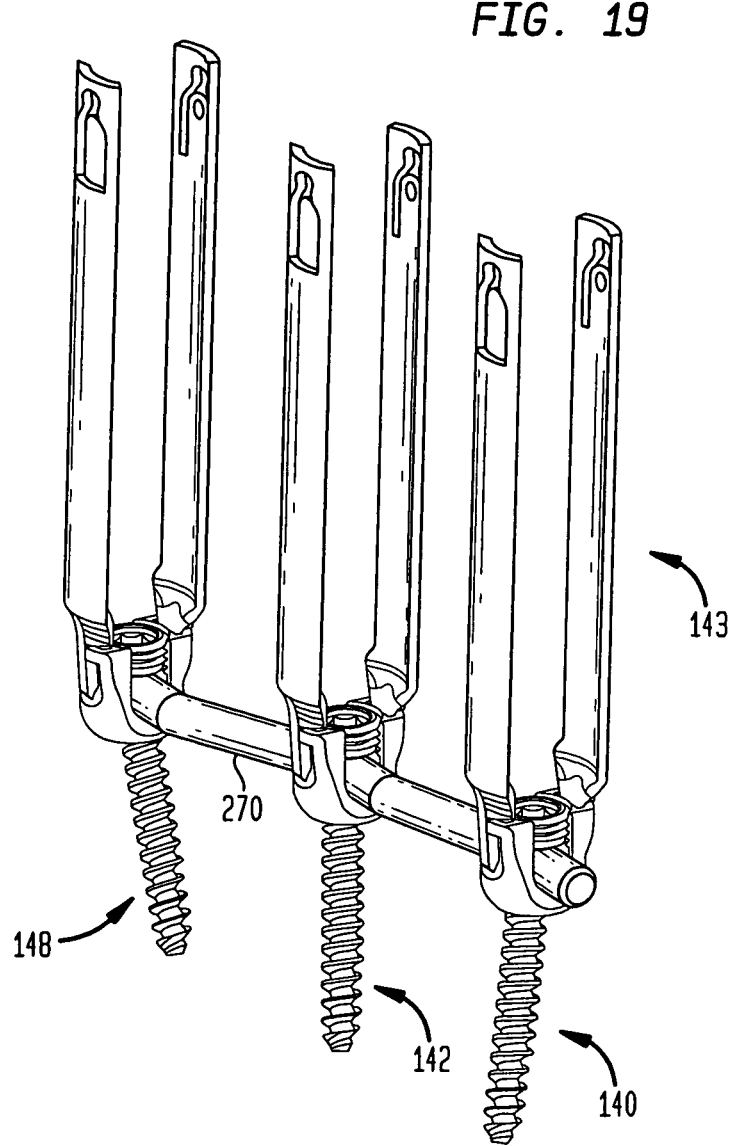
FIG. 19 is a perspective view as in FIG. 18 of the contoured rod fastened to the pedicle screws.
Figure 20:
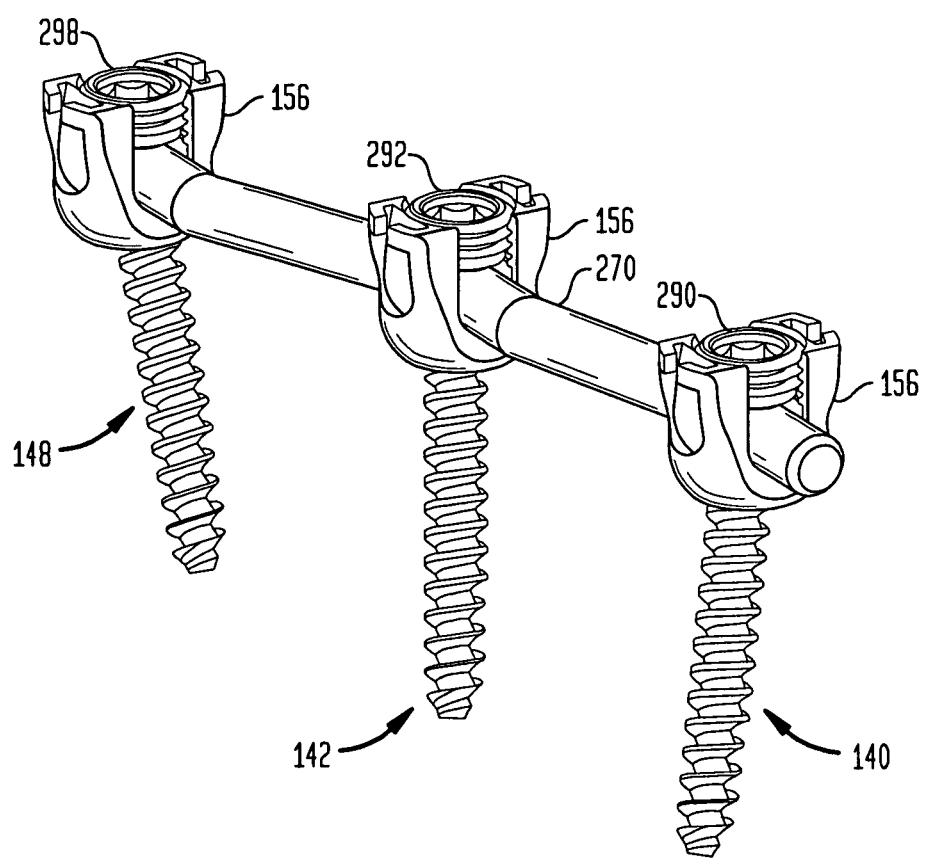
FIG. 20 is a perspective view as in FIG. 19 of the contoured rod fastened to the pedicle screws after removal of the retractor blades.

A typical surgical procedure in accordance with the present invention will now be described. It will be understood by those of ordinary skill in the art that additional or fewer steps may be performed, the sequence of steps can be varied as appropriate and that substitute techniques and methods may be utilized. Nonetheless, during a typical surgery, a surgeon may perform the following steps: percutaneously installing guide wires in bones, such as adjacent vertebrae, as shown in FIG. 1, using blunt dilators and cannulas to open incisions and cavities as shown in FIGS. 2-5, percutaneously installing polyaxial screws with retractor blades attached as shown in FIG. 6, removing the cannulas and guide wires as shown in FIGS. 7 and 7A, installing the abutment members to form slotted cannula assemblies, installing the trough simulation members or rods to the cannula assembly and/or the polyaxial screw head to form contouring assemblies as shown in FIG. 8 and alternatively, in FIG. 17, aligning the contouring assemblies in a parallel relationship and installing the links onto the assemblies as shown in FIG. 9 and, alternately, in FIG. 17, contouring the fixation member to fit the trough simulation members as shown in FIG. 10 or alternatively to fit into the trough simulation rods shown in FIG. 18, installing the contoured fixation member percutaneously as shown in FIG. 11, fastening the fixation member in the polyaxial screws as shown in FIGS. 12, 13 and 19, and removing the elongate members As Shown In FIGS. 14 and 20 and thereafter completing the surgery.

The foregoing description discloses a number of different elements, any of which may be components of a system for configuring or selecting one or more implants for implantation in a body of a patient. Although the foregoing examples relate to the assembly and implantation of a posterior spinal fusion system, the present invention may be applied to a wide variety of implants, within and outside the orthopedic area. The present invention has particular benefits when an implant is to be configured or selected for a given patient, with reference to two or more anatomic points within the body.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for configuring or selecting one or more implants and for implanting the implants proximate a bone in the body of a patient, the system comprising:
    a first cannula having a proximal end and a distal end, the distal end being adapted to engage a first pedicle fastener implantable in a pedicle of a first vertebra of a spine proximate a first anatomic point, the first pedicle fastener having a first trough, the first cannula defining a first slot and a second slot in a side wall thereof, the first and second slots extending along the first cannula between the proximal and distal ends;
    a second cannula having a proximal end and a distal end, the distal end being adapted to engage a second pedicle fastener implantable in a pedicle of a second vertebra of the spine proximate a second anatomic point, the second pedicle fastener having a second trough, the second cannula defining a first slot and a second slot in a side wall thereof, the first and second slots extending along the second cannula between the proximal and distal ends;
    a first simulation member having a proximal end defining a first simulation trough, the first simulation member being configured to attach to the first cannula such that the first simulation trough is positioned outside the body when the first cannula is engaged with the first pedicle fastener implanted in the first vertebra; and
    a second simulation member having a proximal end defining a second simulation trough, the second simulation member being configured to attach to the second cannula such that the second simulation trough is positioned outside the body when the second cannula is engaged with the second pedicle fastener implanted in the second vertebra;
    wherein, when the first and second simulation members are attached to the respective first and second cannulas, the first and second simulation members provide a spatial transformation, whereby the first anatomic point is projected to a first projected point proximate the first simulation trough by a projection distance and the second anatomic point is projected to a second projected point proximate the second simulation trough by the projection distance, and the first and second simulation troughs are arranged to receive a rod in a position extending simultaneously through the first and second projected points.

2. The system of claim 1, wherein the first simulation member is removably attachable to the proximal end of the first cannula, and wherein the second simulation member is removably attachable to the proximal end of the second cannula.

3. The system of claim 2, wherein the first simulation member is removably attachable to the proximal end of the first cannula by a first tab releasably engaged within a first slot, and wherein the second simulation member is removably attachable to the proximal end of the second cannula by a second tab releasably engaged within a second slot.

4. The system of claim 1, wherein the first cannula comprises:
    a first blade; and
    a second blade discrete from the first blade;
    wherein the first and second blades are positionable substantially parallel to each other to provide the first cannula.

5. The system of claim 1, wherein the distal end of the first cannula has a first docking element discrete from and securable to the first pedicle fastener, and wherein the distal end of the second cannula has a second docking element discrete from and securable to the second pedicle fastener.

6. The system of claim 5, wherein the first docking element comprises a plurality of first tabs receivable in corresponding first slots of the first pedicle fastener, and wherein the second docking element comprises a plurality of second tabs receivable in corresponding second slots of the second pedicle fastener.

7. The system of claim 1, wherein the rod is a spinal fusion rod for restricting relative motion between the first and second vertebrae.

8. The system of claim 1, further comprising a first bridge configured to constrain an orientation of the first simulation member with respect to the second simulation member.

9. The system of claim 8, wherein the first bridge is connectable to the first and second simulation members.

10. The system of claim 1, wherein the first simulation member includes a base and a stem, the first simulation trough of the first simulation member being located on the stem of the first simulation member, and wherein the second simulation member includes a base and a stem, the second simulation trough of the second simulation member being located on the stem of the second simulation member.

11. The system of claim 1, further comprising:
    a third cannula having a proximal end and a distal end, the distal end being adapted to engage a third pedicle fastener implantable in a pedicle of a third vertebra of the spine proximate a third anatomic point, the third pedicle fastener having a third trough, the third cannula defining a first slot and a second slot in a side wall thereof, the first and second slots extending along the third cannula between the proximal and distal ends; and
    a third simulation member having a proximal end defining a third simulation trough, the third simulation member being configured to attach to the third cannula such that the third simulation trough is positioned outside the body when the third cannula is engaged with the third pedicle fastener implanted in the third vertebra;
    wherein, when the first, second, and third simulation members are securely coupled with the respective first, second, and third cannulas, the first, second, and third simulation members provide the spatial transformation, whereby the third anatomic point is projected to a third projected point proximate the third simulation trough by the projection distance, and the first, second, and third simulation troughs are arranged to receive the rod in a position extending simultaneously through the first, second, and third projected points.

12. The system of claim 11, further comprising:
    a first bridge configured to constrain an orientation of the first simulation member with respect to the second simulation member; and
    a second bridge configured to constrain an orientation of the second simulation member with respect to the third simulation member.

13. A system for configuring or selecting one or more implants and for implanting the implants proximate a bone in the body of a patient, the system comprising:
    a first passageway device having a proximal end and a distal end and defining a passageway therealong between the proximal and distal ends adapted to receive a spinal fusion rod therein, the distal end being adapted to engage a first pedicle fastener implantable in a pedicle of a first vertebra of a spine proximate a first anatomic point, the first pedicle fastener having a first trough;
    a second passageway device having a proximal end and a distal end and defining a passageway therealong between the proximal and distal ends adapted to receive the spinal fusion rod therein, the distal end being adapted to engage a second pedicle fastener implantable in a pedicle of a second vertebra of the spine proximate a second anatomic point, the second pedicle fastener having a second trough;

a first simulation member having a proximal end defining a first simulation trough, the first simulation member being configured to attach to the first passageway device such that the first simulation trough is positioned outside the body when the first passageway device is engaged with the first pedicle fastener implanted in the first vertebra; and a second simulation member having a proximal end defining a second simulation trough, the second simulation member being configured to attach to the second passageway device such that the second simulation trough is positioned outside the body when the second passageway device is engaged with the second pedicle fastener implanted in the second vertebra;

wherein, when the first and second simulation members are attached to the respective first and second passageway devices, the first and second simulation members provide a spatial transformation, whereby the first anatomic point is projected to a first projected point proximate the first simulation trough by a projection distance and the second anatomic point is projected to a second projected point proximate the second simulation trough by the projection distance, and the first and second simulation troughs are arranged to receive the spinal fusion rod in a position extending simultaneously through the first and second projected points.

14. The system of claim 13, wherein the first simulation member is removably attachable to the proximal end of the first passageway device, and wherein the second simulation member is removably attachable to the proximal end of the second passageway device.

15. The system of claim 14, wherein the first simulation member is removably attachable to the proximal end of the first passageway device by a first tab releasably engaged within a first slot, and wherein the second simulation member is removably attachable to the proximal end of the second passageway device by a second tab releasably engaged within a second slot.

16. The system of claim 13, wherein the first passageway device comprises:
 a first blade; and
 a second blade discrete from the first blade;
 wherein the first and second blades are positionable substantially parallel to each other to define the first passageway device.

17. The system of claim 13, wherein the distal end of the first passageway device has a first docking element discrete from and securable to the first pedicle fastener, and wherein the distal end of the second passageway device has a second docking element discrete from and securable to the second pedicle fastener.

18. The system of claim 17, wherein the first docking element comprises a plurality of first tabs receivable in corresponding first slots of the first pedicle fastener, and wherein the second docking element comprises a plurality of second tabs receivable in corresponding second slots of the second pedicle fastener.

19. The system of claim 13, further comprising a first bridge configured to constrain an orientation of the first simulation member with respect to the second simulation member.

20. The system of claim 19, wherein the first bridge is connectable to the first and second simulation members.

21. The system of claim 13, wherein the first simulation member includes a base and a stem, the first simulation trough of the first simulation member being located on the stem of the first simulation member, and wherein the second simulation member includes a base and a stem, the second simulation trough of the second simulation member being located on the stem of the second simulation member.

22. The system of claim 13, further comprising:
 a third passageway device having a proximal end and a distal end, the distal end being adapted to engage a third pedicle fastener implantable in a pedicle of a third vertebra of the spine proximate a third anatomic point, the third pedicle fastener having a third trough; and
 a third simulation member having a proximal end defining a third simulation trough, the third simulation member being configured to attach to the third passageway device such that the third simulation trough is positioned outside the body when the third passageway device is engaged with the third pedicle fastener implanted in the third vertebra;
 wherein, when the first, second, and third simulation members are securely coupled with the respective first, second, and third passageway devices, the first, second, and third simulation members provide the spatial transformation, whereby the third anatomic point is projected to a third projected point proximate the third simulation trough by the projection distance, and the first, second, and third simulation troughs are arranged to receive the rod in a position extending simultaneously through the first, second, and third projected points.

23. The system of claim 22, further comprising:
 a first bridge configured to constrain an orientation of the first simulation member with respect to the second simulation member; and
 a second bridge configured to constrain an orientation of the second simulation member with respect to the third simulation member.

* * * * *